US012667712B2

(12) United States Patent
Spanier et al.

(10) Patent No.: US 12,667,712 B2
(45) Date of Patent: Jun. 30, 2026

(54) METHODS FOR PROVIDING VENTRICULAR SUPPORT FOR A HUMAN PATIENT

(71) Applicant: ABIOMED, INC., Danvers, MA (US)

(72) Inventors: Gerd Bruno Spanier, Aachen (DE); Joerg Schumacher, Aachen (DE); Christopher Zarins, Danvers, MA (US); Ralph Louis D'Ambrosio, Danvers, MA (US); Samantha Polak, Danvers, MA (US); Yonghong Gao, Danvers, MA (US); Mariah Hout, Danvers, MA (US); John Kenneth Ryder, Danvers, MA (US); Noam Josephy, Danvers, MA (US); David Weber, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 19/078,868

(22) Filed: Mar. 13, 2025

(65) Prior Publication Data

US 2025/0288791 A1 Sep. 18, 2025

Related U.S. Application Data

(60) Provisional application No. 63/770,664, filed on Mar. 12, 2025, provisional application No. 63/566,159, filed on Mar. 15, 2024.

(51) Int. Cl.
*A61M 60/17* (2021.01)
*A61M 60/13* (2021.01)
(Continued)

(52) U.S. Cl.
CPC ............ *A61M 60/17* (2021.01); *A61M 60/13* (2021.01); *A61M 60/35* (2021.01);
(Continued)

(58) Field of Classification Search
CPC .. A61M 60/17; A61M 60/585; A61M 60/411; A61M 60/35; A61M 60/13; A61M 60/126; A61M 60/865
See application file for complete search history.

(56) References Cited

U.S. PATENT DOCUMENTS 10,842,498 B2 * 11/2020 Vale ................. A61B 17/12118
10,842,562 B2 * 11/2020 Zhang ................ A61B 18/1492
(Continued)

FOREIGN PATENT DOCUMENTS

EP          3618884 B1    11/2021
WO     2019-035804 A1     2/2019

OTHER PUBLICATIONS

International Written Opinion and Search Report issued in PCT/US2025/019808 dated Jun. 27, 2025.

*Primary Examiner* — Pamela M. Bays
(74) *Attorney, Agent, or Firm* — TROUTMAN PEPPER LOCKE LLP

(57) ABSTRACT

A method of providing ventricular support for a human patient during a high-risk percutaneous coronary intervention procedure includes inserting a mechanical circulatory support device into the vasculature of a human patient. The mechanical circulatory support device being movable between a compressed state and an expanded state. The mechanical circulatory support device is delivered into a heart of the human patient with the aid of a delivery assist device. Operating. The mechanical circulatory support device is operated for a support period. A clinically significant arrhythmia adverse event (AE) associated with the mechanical circulatory support device experiencing the arrhythmia event between the time of vascular access with the mechanical circulatory support device and removal of
(Continued)

the mechanical circulatory support device from the vasculature is approximately 2.3%.

13 Claims, 7 Drawing Sheets

(51) Int. Cl.

| | |
|---|---|
| *A61M 60/35* | (2021.01) |
| *A61M 60/411* | (2021.01) |
| *A61M 60/585* | (2021.01) |
| *A61M 60/126* | (2021.01) |
| *A61M 60/865* | (2021.01) |

(52) U.S. Cl.
CPC ........ *A61M 60/411* (2021.01); *A61M 60/585* (2021.01); *A61M 60/126* (2021.01); *A61M 60/865* (2021.01)

(56) References Cited

U.S. PATENT DOCUMENTS

| | | | | |
|---|---|---|---|---|
| 11,071,585 | B2 * | 7/2021 | Zhang | ................ A61B 18/1492 |
| 12,076,037 | B2 * | 9/2024 | Brady | ..................... A61F 2/013 |
| 2008/0132748 | A1 * | 6/2008 | Shifflette | ............ A61M 60/865 |
| | | | | 600/16 |
| 2019/0216995 | A1 * | 7/2019 | Kapur | .................. A61M 60/117 |
| 2020/0405926 | A1 | 12/2020 | Alexander et al. | |
| 2021/0093836 | A1 | 4/2021 | Fantuzzi | |
| 2023/0056430 | A1 * | 2/2023 | Kadrolkar | ............ A61B 5/7282 |
| 2023/0086096 | A1 | 3/2023 | Siess et al. | |

* cited by examiner

FIG. 6

| | Total Investigated Events | | Vascular access to prior to PCI initiation | | PCI initiation to device removal | |
|---|---|---|---|---|---|---|
| | Events n=57 | Subjects n=52 | Events n=44 | Subjects n=42 | Events n=13 | Subjects n=10 |
| i. Repositioning | 28 | 28 | 27 | 27 | 1 | 1[5] |
| ii. Arrhythmia due to the ECP meeting the protocol definition of a sustained arrhythmia or causing hemodynamic compromise | 8 | 5 | 3 | 3 | 5 | 2[6] |
| iii. Pump requiring replacement | 4 | 4 | 4 | 4 | 0 | 0 |

FIG. 7

| | Pre-Specified Study Analysis | | | | |
| --- | --- | --- | --- | --- | --- |
| | Rate of Arrhythmia | Device Repositioning | Device Removal | Site Reported Arrhythmia AEs[9] | Sustained Arrhythmia[2] |
| Ventricular Arrhythmia Assessment | 57% (145/256) | 19% (48/256) | 0% (0/256) | 23% (59/256) | 2.7% (7/256) |

| | Post-Hoc Analysis | | | |
| --- | --- | --- | --- | --- |
| | Rate of Arrhythmia[13] | Device Repositioning | Device Removal | Sustained Arrhythmia or Hemodynamic Compromise[14] |
| Subjects with events occuring from Vascular Access to Device Removal | 16% (42/256) | 11% (28/256) | 1.6% (4/256) | 2.0% (5/256) |
| Subjects with events occuring during PCI | 3.9% (10/256) | .4% (1/256) | 0% (0/256) | .8% (2/256) |

| Comparator Studies[15] | Rate of Site Reported AE Terms "cardiopulmonary resuscitation (SPR) or Ventricular Arrhythmia" [In-Hospital] | Rate of Site Reported AE Term "Ventricular Arrhythmia requiring cardioversion" [during device support] |
| --- | --- | --- |
| Protect II | | |
| Impella 2.5 | | 2.2% (5/225) |
| IABP[16] | | 1.3% (3/223) |
| Protect III | | |
| Impella 2.5 | 2.4% (9/372) | |
| Impella CP | 1.9% (16/864) | |

METHODS FOR PROVIDING VENTRICULAR SUPPORT FOR A HUMAN PATIENT

CROSS-REFERENCE TO RELATED APPLICATIONS

The present application claims priority to U.S. Provisional Application Ser. No. 63/566,159 filed Mar. 15, 2024. The present application also claims priority to U.S. Provisional Application Ser. No. 63/770,664 filed Mar. 12, 2025. The above applications are incorporated herein in their entirety.

TECHNICAL FIELD

Disclosed herein are methods for providing ventricular support for human patients.

BACKGROUND

Mechanical circulatory support devices, such as intracardiac or intravascular blood pumps may be introduced in the heart to deliver blood from the heart into an artery. Such devices are often introduced to support the function of the heart after a patient suffers a cardiac episode. One such class of devices is the Impella® line of blood pumps. Some blood pump assemblies may be introduced percutaneously through the vascular system during a cardiac procedure. Specifically, blood pump assemblies can be inserted via a catheterization procedure through the femoral artery or the axillary/subclavian artery, into the ascending aorta, across the aortic valve and into the left ventricle. The inserted blood pump assembly may be configured to pull blood from the left ventricle of the heart through a cannula and expels the blood into the aorta. A blood pump assembly may also be configured to pull blood from the inferior vena cava and to expel blood into the pulmonary artery. Some mechanical circulatory support devices are powered by an on-board motor, while others are powered by an external motor and a drive cable.

BRIEF SUMMARY

The present disclosure describes systems, devices, and methods of providing ventricular support during a high-risk percutaneous coronary intervention procedure.

One aspect of the present disclosure relates to a method of providing ventricular support for human patients during a high-risk percutaneous coronary intervention procedure. The method comprising: inserting a mechanical circulatory support device into the vasculature of a human patient; delivering the mechanical circulatory support device within the vasculature into a heart of the human patient; operating the mechanical circulatory support device for a support period of up to 6 hours; and wherein a rate of incidence of a major adverse cardiovascular and cerebrovascular event ("MACCE") is identified during an assessment period beginning from the insertion of the mechanical circulatory support device into the vasculature of the human patient through about 30 days after the high-risk percutaneous coronary intervention procedure, the composite rate of MACCE during the assessment period being approximately 5.9% to approximately 12.9%.

Another aspect of the present disclosure relates to a method of providing ventricular support for a human patient during a high-risk percutaneous coronary intervention procedure, the method comprising: inserting a mechanical circulatory support device into the vasculature of a human patient, the mechanical circulatory support device being movable between a compressed state and an expanded state; delivering, with the aid of a delivery assist device, the mechanical circulatory support device into a heart of the human patient; operating the mechanical circulatory support device for a support period; and wherein a clinically significant arrhythmia adverse event (AE) associated with the mechanical circulatory support device experiencing the arrhythmia event between the time of vascular access with the mechanical circulatory support device and removal of the mechanical circulatory support device from the vasculature is approximately 2.3%.

BRIEF DESCRIPTION OF DRAWINGS

The foregoing and other objects and advantages will be apparent upon consideration of the following detailed description, taken in conjunction with the accompanying drawings, in which like reference characters refer to like parts throughout, and in which:

FIG. 6 is a table illustrating the Impella ECP™ Pivotal Study Repositioning, Arrhythmia and Replacement; and FIG. 7 is a table illustrating the Impella ECP™ Arrhythmia Analysis Comparison to Previous Impella Studies.

DETAILED DESCRIPTION

Figure 1:
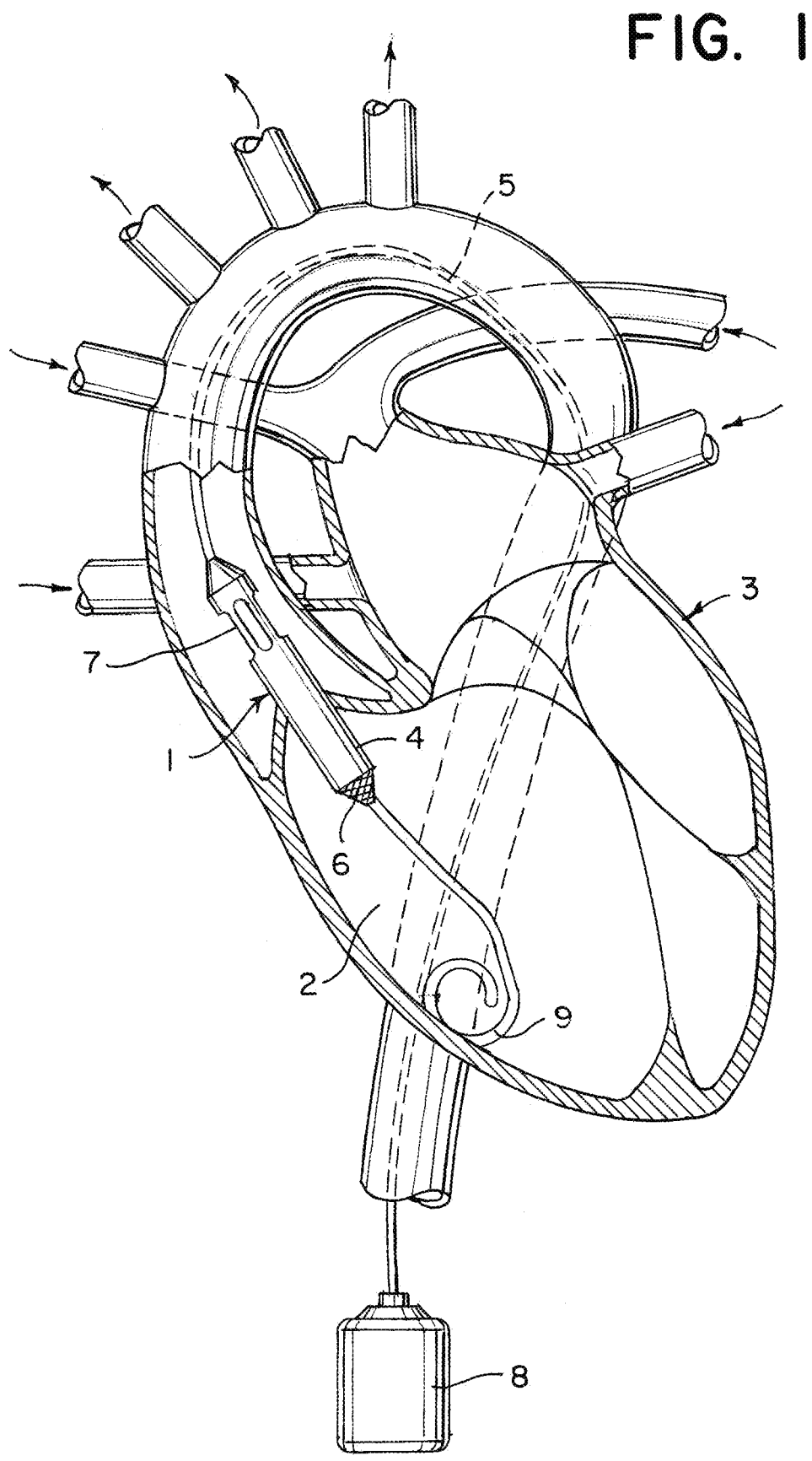
FIG. 1 illustrates an exemplary intravascular blood pump positioned within a left ventricle of a heart in accordance with aspects of the present technology.

Aspects of the present disclosure are described in detail with reference to the drawing figures wherein like reference numerals identify similar or identical elements. It is to be understood that the disclosed aspects are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items. In the claims, as well as in the specification above, all transitional phrases such as "comprising," "including", "carrying", "having", "containing", "involving", "holding", "composed of", and the like are to be understood to be open-ended, i.e., to mean including but not limited to. Only the transitional phrases "consisting of" and "consisting essentially of" shall be closed or semi-closed transitional phrases, respectively.

As used herein, the terms "proximal" and "distal" refer to positions relative to a physician or operator of the intravascular blood pump. Thus, "proximal" indicates a position that is closer to the physician or operator or a direction that points towards the physician or operator, and "distal" indicates a position that is farther from the physician or operator or a direction that points away from the physician or operator.

As used herein, "operator" can include a doctor, surgeon, or any other individual or instrumentation associated with delivery and operation of a mechanical circulatory support device in a human patient.

As used herein, the term "percutaneous coronary intervention" (PCI) refers to a non-surgical procedure used to treat the blockages in a coronary artery. PCI opens up narrowed or blocked sections of the artery, restoring blood flow to the heart.

As used herein, sustained arrhythmia refers to ventricular fibrillation, ventricular tachycardia, higher degree conductive disorder or newly developed atrial fibrillation lasting >60 seconds and requiring cardioversion/defibrillation and/or IV amiodarone_during placement of support with or removal of the device.

As used herein clinically significant arrhythmia adverse event (AE) refers to patients having an arrhythmia during the time from vascular access through device removal and having one of the following:

Arrhythmia AE requiring repositioning of the device during the PCI;

Arrhythmia AE caused by the device that met the definition of a sustained arrhythmia or resulted in hemodynamic compromise; or Arrhythmia resulting in device removal.

Sustained arrhythmia is ventricular fibrillation, ventricular tachycardia, higher degree conductive disorder or newly developed atrial fibrillation lasting >60 seconds and requiring cardioversion/defibrillation and/or IV amiodarone during placement of support with or removal of the device.

As used herein hemodynamic compromise is defined as the use of inotropes or vasopressors by a patient.

As used herein, temporary ventricular support refers to ventricular support to patients during high-risk PCI for 6 hours or less (≤6 hours).

As used herein, the term "major adverse cardiovascular and cerebrovascular event (MACCE)" refers to one of death, stroke, myocardial infarction, target vessel repeat revascularization, or any combination thereof.

As described herein, PCI is a nonsurgical procedure used to treat the blockages in a coronary artery. PCI opens up narrowed or blocked sections of the artery, restoring blood flow to the heart. It is performed in the catheterization lab by an interventional cardiologist. The purpose of the procedure is to open up narrowed arteries using either a stent and/or balloon angioplasty. PCI techniques have evolved over the past two decades as a result of advances in available technology and greater operator expertise. As a result, the indication for PCI has evolved from simple, discrete lesions in patients with single-vessel disease and well-preserved left ventricular function to multiple, complex lesions in sicker patients with complex coronary anatomy, depressed left ventricular function and advanced comorbidities. Coronary artery bypass grafting (CABG) is a procedure to improve blood flow to the heart by opening up narrowed arteries and/or blocked arteries. Both PCI and/or CABG are used during revascularization procedures.

Patients in need of revascularization procedures often present with very high-risk features, including but not limited to complex pathologic multivessel coronary anatomy, depressed left ventricular function and advanced comorbidities. Historically, CABG has been the recommended approach for revascularization procedures for patients with multivessel disease and depressed left ventricular function, especially in patients who may also have angina or heart failure symptoms. However, patients exhibiting these symptoms may be very sick and thus, CABG may increase the risk of mortality and/or morbidity. In such instances, PCI may be the only viable alternative to executing a revascularization procedure for high-risk patients.

During such PCI procedures, many techniques are used to transiently interrupt blood flow within the target coronary artery. Such techniques may include repetitive contract dye injections, balloon inflations, atherectomy passes and stents. By using these techniques, the patient may experience ischemic and diastolic dysfunction. The patient may also later experience myocardial ischemia, which may result in decreased cardiac output and thus decreased coronary flow. Furthermore, in patients with poor cardiac reserve, the risk of immediate or delayed hemodynamic compromise or collapse is the highest. Thus, it may be necessary to hemodynamically support the patient's heart during a PCI procedure.

One way of providing such hemodynamic support during a PCI procedure is by using a suitable mechanical circulatory support device. An example of a suitable mechanical circulatory support device is a transvalvular microaxial pump (e.g., Impella® line of blood pumps, or similar devices), where the pump is inserted percutaneously or surgically into the aorta and across the aortic valve, and pumps blood out of the left ventricle and into the aorta. Examples of such suitable mechanical circulatory support devices include both the Impella 2.5® blood pump and the Impella CP® blood pump (Abiomed, Danvers, Mass.) In both such examples, blood may be drawn through the cannula situated in the left ventricle and expelled into the aorta. Both the Impella 2.5 and the Impella CP have continuous pump flows up to 2.5 and 3.8 liters per minute, respectively.

Impella is incorporated into eight medical guidelines for multiple indications, including PCI procedures. Specifically, there is support for the use of Impella in patients with reduced or normal left ventricular function and severe coronary artery disease for treatment of anticipated technically challenging or prolonged PCI procedures. The Impella 2.5 and Impella CP ventricular support systems are approved by the FDA for providing temporary (≤6 hours) ventricular support to patients during high-risk PCI.

Existing transvalvular microaxial pumps, such as Impella 2.5 and Impella CP, require a relatively large bore (at least a 12 French) femoral access site for device placement. As used herein, a measurement of 1 French (Fr) is equivalent to ⅓ millimeter (mm). The bore access site size is primarily limited by the motor body size of the device. In some instances, a relatively large bore access site may be more susceptible to bleeding, vascular dissection or ischemia during access and/or closure of the access site than a comparatively smaller bore access site. A mechanical circulatory support device with a flow rate that is comparable to currently available mechanical circulatory support devices, but with a smaller bore access site may be advantageous, especially for short-term procedures such as a PCI. An example of such a mechanical circulatory support device is the Impella ECP™. Disclosed herein is a method of using such a mechanical circulatory support device for providing ventricular support to patients during high-risk PCI, resulting in an acceptable rate of incidence of major adverse cardiovascular and cerebrovascular event (MACCE).

A clinically significant arrhythmia adverse event (clinically significant arrhythmia AE) associated with the mechanical circulatory support device is a patient experiencing an arrhythmia AE event between the time of vascular access with the mechanical circulatory support device and removal of the mechanical circulatory support device from the vasculature. In accordance with the disclosed technology, the clinically significant arrhythmia AE is approximately 2.3%, for example, while supporting a patient with the mechanical circulatory support device as discussed herein.

The Impella ECP™ blood pump is a percutaneous transvalvular microaxial blood pump that allows the pump head or section to be radially compressed to reduce the pump head diameter prior to insertion to permit device placement through smaller access sites. For example, the Impella ECP™ blood pump may be compressed (e.g., using a crimping tool) and inserted in the compressed state percutaneously through an introducer sheath placed in the femoral artery. After insertion and placement, the Impella ECP™ blood pump may radially expand to an outer diameter of 21 Fr and deliver a maximum flow rate of 4.4 L/min.

Figures 2, 3B:
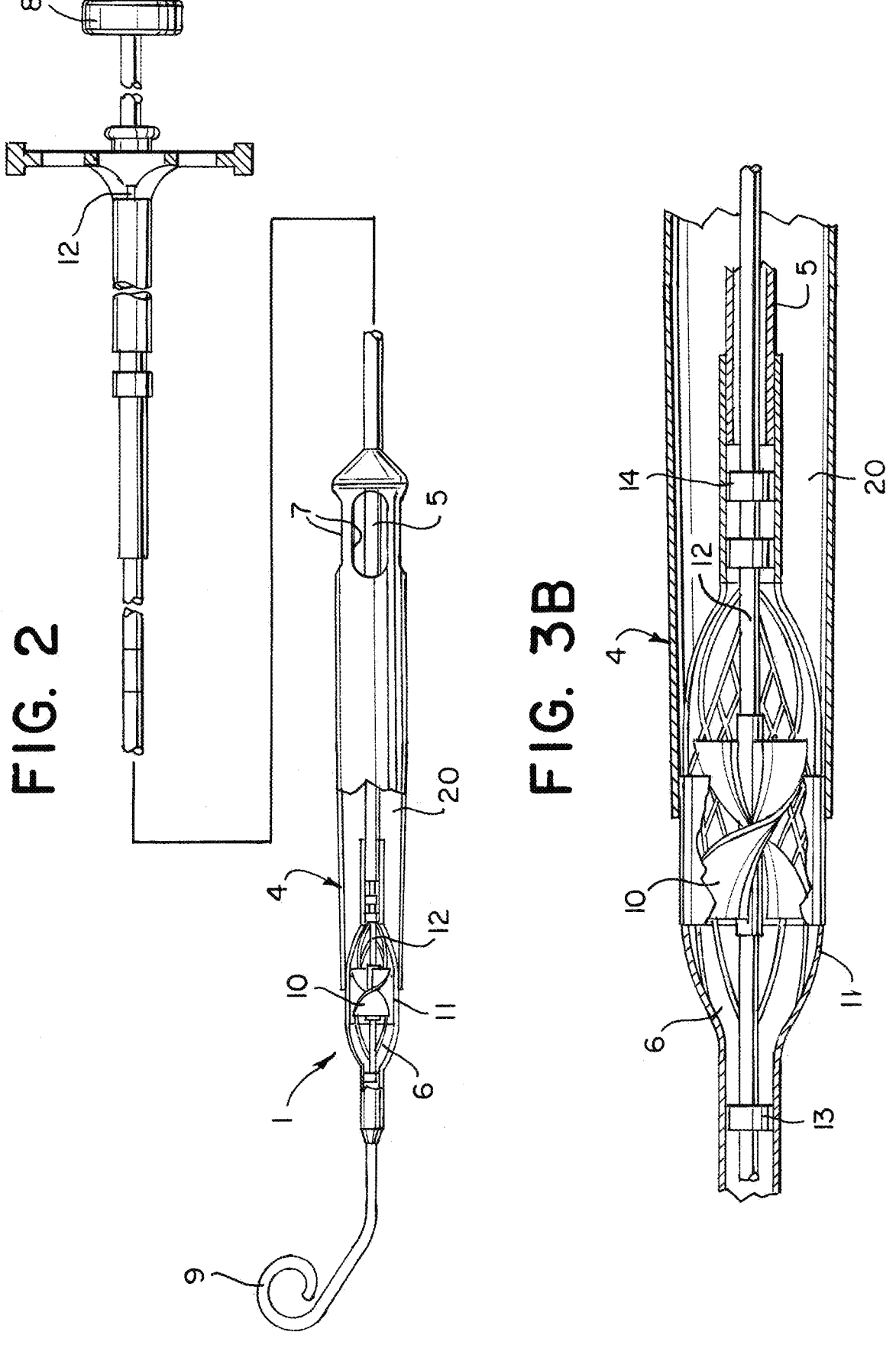
FIG. 2 illustrates a side view of the exemplary intravascular blood pump of FIG. 1 in accordance with aspects of the present technology.
Figures 3A, 3B:
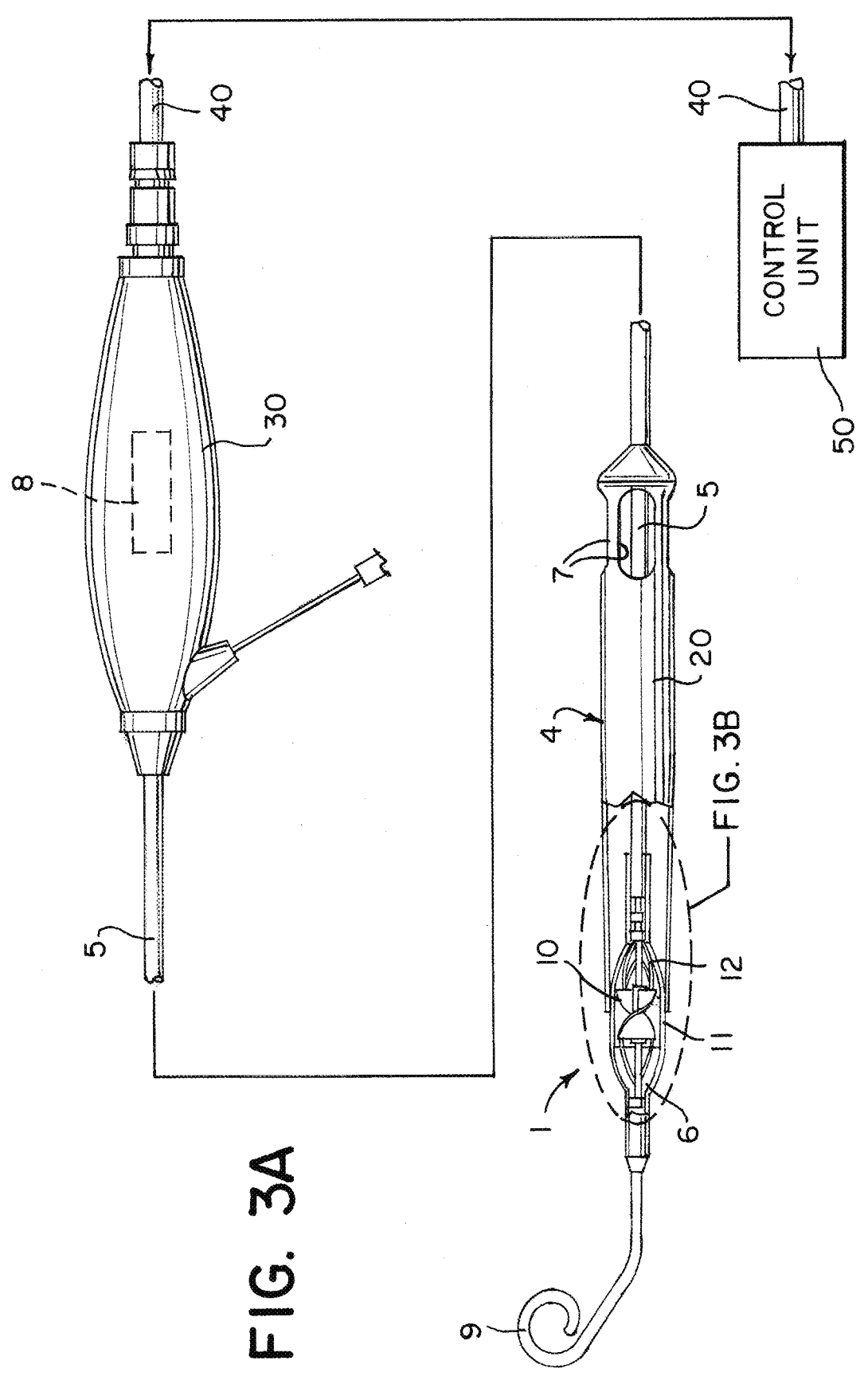
FIG. 3 illustrates a side view of the exemplary intravascular blood pump of FIG. 1 including a cross-section of a distal portion of the intravascular pump of FIG. 1 in accordance with aspects of the present technology.

For example, FIGS. 1-3 illustrate a mechanical circulatory support device that is an intravascular blood pump 1 for mechanically supporting a left ventricle 2 of a human heart 3 according to some aspects of the present technology. As described in greater detail herein, the blood pump 1 is radially compressible to permit device placement through smaller access sites, e.g., through a 9 Fr introducer sheath placed in the femoral artery.

It is to be appreciated that the intravascular blood pump 1 may include at least some of the features of the Impella ECP™ blood pump and pump 1 may be used in any of the systems, methods, and procedures described herein.

As shown in FIGS. 1-3, in some aspects, the intravascular blood pump 1 may include a catheter 5 and a pump section 4 mounted at a distal end region of the catheter 5. The pump section 4 may comprise a rotor 10, housing 11, and downstream tubing or outflow tube 20. The intravascular blood pump 1 may be placed inside the human heart 3 using a percutaneous, transluminal technique. As described in greater detail below, the pump section 4 of the intravascular blood pump 1 may be radially compressed to a compressed state, e.g., using a crimping tool and inserted percutaneously through a 9 Fr introducer sheath placed in an access site. For example, the intravascular blood pump 1 may be introduced through, for example, a femoral artery or radially (wrist). Likewise, the intravascular blood pump 1 may be introduced through other vessels, such as through the subclavian artery. As shown in FIG. 1, the catheter 5 may be advanced into the aorta such that the pump section 4 reaches through the aortic valve into the left ventricle 2 of the heart 3.

The pump section 4 may further comprise a rotor 10 (shown in FIGS. 2 and 3) to cause blood to flow from a blood flow inlet 6 at a distal end of the pump section 4 to a blood flow outlet 7 located proximally of the blood flow inlet 6. By placing the blood flow inlet 6 inside the left ventricle 2 and the blood flow outlet 7 inside the aorta, the intravascular blood pump 1 may support the patient's systemic blood circulation. It is to be appreciated that, if the intravascular blood pump 1 is configured and placed differently, it may be used, e.g., to support the patient's pulmonary blood circulation instead.

The catheter 5 may further house a drive shaft 12 (shown in FIGS. 2 and 3) configured to be driven by an electric motor 8, which may be positioned outside the patient's body. The drive shaft 12 may be configured to drive rotor 10 contained inside the pump section 4.

As shown in FIGS. 1-3, the pump section 4 may also have a flexible atraumatic tip 9. The flexible tip 9 may be located at the distal end of the pump section 4. In some aspects, the proximal end of tip 4 is coupled to and extends from the distal end of housing 11. The flexible atraumatic tip 9 may have any suitable shape, such as a pigtail or a J-form, and may be configured to facilitate placement of the intravascular blood pump 1 by aiding navigation inside the patient's vascular system. In some embodiments, the flexible tip 9 may form a closed-loop shape. Furthermore, the softness of the flexible atraumatic tip 9 may be configured to allow the pump section 4 to support itself atraumatically against a wall of the left ventricle 2. In some aspects, the atraumatic tip 9 may have variable stiffness. In some aspects, the intravascular blood pump 1 may not include a flexible tip 9.

As shown in FIG. 2, rotor 10 may be located inside a housing 11. In some aspects, the housing 11 may form a cage around the rotor 10. In some aspects, both the rotor 10 and the housing 11 may be made of material(s) and/or have a structure configured such that the rotor 10 and housing 11 are configured to be compressible. In such aspects, the intravascular blood pump 1 may be inserted into and/or through the patient's vascular system while either both the rotor 10 and/or the housing 11 are in their compressed state, and such that the rotor 10 and housing 11 may be expanded once the pump section 4 is positioned at or near its target location in the patient's heart 3. For example, in some aspects, expansion may occur when the housing 11 is in the ventricle 2, the ascending aorta, or the descending aorta. Likewise, in some aspects, expansion may occur directly after the housing 11 is introduced into the patient's vasculature, with the housing 11 then being moved to its target location in the patient's heart 3 in its expanded state. As will be appreciated, expansion may occur in any suitable location within the patient's vasculature, such as a portion of the patient's vasculature having a diameter that exceeds the diameter of the expanded housing 11. In some aspects, the rotor 10 and housing 11 may be formed from any suitable material or materials. For example, in some aspects of the technology, the rotor 10 and/or housing 11 may be made at least in part from polyurethane, silicone rubber, a shape-memory material such as Nitinol or Ultra-Stiff Nitinol ("USN"), etc.

The drive shaft 12 may extend through the entire catheter 5 or only parts thereof. In some aspects, the drive shaft 12 may be hollow along all or a portion of its length. The drive shaft 12 or portions thereof may be formed from a cable, solid shaft, hollow shaft, or combinations thereof. In that regard, the drive shaft 12 may be a flexible cable formed of any suitable number of differently oriented fiber layers (e.g., 2 layers, 3 layers, 4 layers, etc.). For example, the drive shaft 12 may be formed from a plurality of coaxial windings, each with different or alternating winding directions. In such an example, the different or alternating winding directions may be running helically around a lumen extending axially along the drive shaft 12. In some aspects of the technology, the drive shaft 12 may include two coaxial windings, each with opposite winding directions, and an outer diameter of the drive shaft 12 may be between 0.4 mm and 2 mm, preferably between 0.6 mm and 1.2 mm, particularly preferably between 0.8 mm and 1.0 mm. In cases where the drive shaft 12 has at least one outer layer and/or inner layer which includes a winding or windings, each wire of the winding may comprise one strand or several strands, e.g. that may be twisted. In some cases, the windings of a given layer may form a single helix. Likewise, in some cases, the windings of a given layer may include two or more helices which are preferably shifted axially, similar to a multistart thread. In some cases, the drive shaft 12 may include one or more layers of braided wire, similar to the outer sheath of a kernmantle rope. In all cases, the wire(s) of a given layer may be formed from any suitable metal or other material, and may further include one or more surface coatings.

As shown in the example of FIG. 2, the proximal end of the drive shaft 12 may be attached to an extracorporeal electric motor 8. In such a configuration, the drive shaft 12 may run through catheter 5, protrude from a distal end of the catheter 5, and serve to transfer torque from the electric motor 8 to the rotor 10 at the distal end of the drive shaft 12. In some aspects of the technology, the drive shaft 12 may include a stiff, rigid, and/or reinforced section at its distal end, onto which the rotor 10 is attached inside the housing 11, in order to provide stability and to mount the rotor 10 within housing 11. Rotor 10 may be configured such that, when it is rotated by the drive shaft 12, blood is drawn into the blood flow inlet 6 at the distal end of the housing 11, and pumped through the housing 11 into a downstream tubing or outflow tube 20, which is attached to the housing 11 and extends proximally. The blood may then be ejected from the outflow tube 20 through a blood flow outlet 7 provided toward the proximal end of the outflow tube 20. The blood flow outlet 7 may have a single opening, or any suitable number of openings.

In some aspects of the technology, the outflow tube 20 may be made of a flexible material or materials such that it may be radially compressed by the aortic valve as the patient's heart 3 is pumping. Likewise, in some aspects of the technology, the outflow tube 20 may be configured to expand as a result of a blood flow generated by the rotor 10 during rotation.

In some aspects of the present technology, pump housing 11 is a frame structure that is formed by a mesh with openings which may, at least in part, be covered by an elastic material. For example, in one aspect, a central portion of the frame structure is covered by a coating leaving exposed openings of the frame structure distal and proximal to the coating on the central portion. A proximal portion of pump housing 11 extends into and is mounted (e.g., to the distal end of catheter 5) in the hollow interior of outflow tube 20. The distal portion of pump housing 11 extends distally beyond the distal end of outflow tube 20. In some aspects, the exposed openings in the mesh pump housing 11 extending distally beyond outflow tube 20 form the inlet 6 of pump 1. The proximal end (or a portion proximate to the proximal end) of outflow tube 20 includes a one or more openings that form the outlet 7 of pump 1. Rotor 10 is mounted to a distal end of drive shaft 12 between distal bearing 13 and proximal bearing 14. Bearings 13 and 14 couple the distal end portion of drive shaft 12 to housing 11 such that drive shaft 12 (and rotor 10) are rotatable relative to housing 11. It is to be appreciated that drive shaft 12 is also rotatable relative to catheter 5. In some aspects, as shown in FIG. 3, the motor 8 is integrated into a handle 30 that is disposed exterior to the patient when the distal portion of pump 1 is deployed within the patient. The drive shaft 12 extends through catheter 5, through the hollow interior of outflow tube 20, into handle 30 and is coupled to motor 8 within handle 30. The proximal end of handle 30 is coupled via cable 40 to control unit 50. Cable 40 may include one or more wires, conductors, etc., for connecting motor 8 and other components within handle 30 and/or pump 1 to control unit 50.

In some aspects of the present technology, the control unit 50 is configured to provide power to and control the operation of pump 1. For example, the control unit 50 may be configured to control the operation of motor 8 to selectively control rotation (i.e., rotational direction and speed) of drive shaft 12 and thereby control rotation of rotor 10. Control unit 50 may include one or more processors, user interface components, sensors (e.g., one or more current sensors), memory, etc., for controlling operation of pump 1 amongst other functions. In one aspect, control unit 50 may be an Automated Impella Controller® from Abiomed, Inc., Danvers, MA or another control unit with similar features.

As previously described, pump 1 is insertable into the patient's body, e.g., into a left ventricle 2 of the heart 3, with an introducer system. Housing 11, rotor 10, and outflow tube 20 are radially compressible from an expanded state to a compressed state to permit pump 1 to achieve a relatively small outer diameter of, for example, 9 Fr (3 mm) during insertion. In some aspects, prior to insertion and advancement of pump 1 into the patient's body, pump 1 is crimped from an expanded state to a compressed state. For example, in some aspects, a crimping tool may be used to crimp pump 1 from an expanded state to a compressed state. Then, in the compressed state, pump 1 is advanced through an introducer sheath (e.g., a 9 Fr introducer sheath) that is inserted through an access site into the patient. For example, the pump 1 may be introduced through a femoral artery or other vessels, such as through the subclavian artery. It is to be appreciated that, in some aspects, a transfer sheath may be used to transfer pump 1 in a compressed state from the crimping tool to the introducer sheath. Compressible blood pumps and use of a crimping tool, transfer sheath, and introducer sheath for inserting compressible blood pumps into a patient are discussed in greater detail in U.S. Patent Application Publication No. US 2022/0203084, the entire contents of which are hereby incorporated by reference herein. An exemplary introducer sheath assembly for use with a blood pump is described in greater detail in U.S. Patent Application Publication No. US 2022/0032037, the entire contents of which are hereby incorporated by reference herein.

The Study Protocol is described in "Use of the Impella ECP™ in Patients Undergoing an Elective or Urgent High-Risk Percutaneous Coronary Intervention" the entirety of which is incorporated herein by reference and included in Appendix A attached hereto.

Study data of from the Study Protocol are included in Appendix B filed herewith, the entirety of which is incorporated herein by reference.

U.S. Pat. Nos. 8,439,859, 9,974,893, 10,709,828, 10,478, 538, 8,721,516, 9,771,801, 10,478,540, 11,219,755, 11,793, 997, and US Patent Publication Nos. 2022/0288381, 2023/ 0063196, 2020/0197585, 2022/0203084, 2020/0390953, 2022/0032037 the entireties of each of which is incorporated herein by reference and included in Appendix C filed herewith.

Appendix D is entitled "Appendix G-Arrhythmia Sub-Analyses" and outlines an analysis on arrhythmia events seen during the Impella ECP™ Pivotal study, which is discussed herein. The entirety of Appendix D is incorporated herein by reference.

Percutaneous insertion of the pump 1 into the patient may be performed under fluoroscopy to permit observation of the position of the pump 1 within the patient and aid appropriate positioning of the pump 1. In some aspects, a delivery assist device (or several delivery assist devices) may be used to aid in delivering the pump 1 to a desired location within the patient. For example, the delivery assist device may be used to aid in delivering the pump 1 to a location as shown in FIG. 1 with the outflow tube 20 across the aortic valve and the inlet 6 in the left ventricle 2 of the heart 3 and the outlet 7 in the aorta. The delivery assist device may be any device (or devices) configured to be inserted into the patient and to aid in the delivery of the pump 1 to a desired location within the patient. In some embodiments, the delivery assist device(s) may be configured to hold open an aortic valve leaflet of the patient as the pump 1 crosses the aortic valve. The delivery assist device may be inserted through the same introducer sheath as the pump 1 or through a separate access site or device. The delivery assist device may be inserted together (e.g., in parallel) or separately from the pump 1 through the introducer sheath. In some aspects, the delivery assist device may be inserted adjacent the pump 1 through the introducer sheath. In some aspects, the delivery assist device may be configured to aid in the delivery of the pump 1 to the desired location within the patient such that the pump 1 may not advance over the delivery assist device when inserting the pump 1 and the delivery assist device into the patient. The delivery assist device(s) may comprise any of one or more of guidewires, a secondary or companion catheter (separate from catheter 5) that may be steerable, or any other type of delivery assist device. In some aspects, where the delivery assist device comprises one or more of guidewires, the pump 1 may not advance over the one or more of guidewires, but rather, the pump 1 may be adjacent to the one or more of guidewires during the delivery of the pump 1 to the desired location in the patient. In some aspects, where the delivery assist device comprises a secondary or companion catheter, the distal end of the secondary catheter may be formed as an atraumatic tip having a predetermined shape and stiffness to aid delivery and positioning of pump 1. For example, the distal end of the secondary catheter may be formed in a pigtail shape (or other shape). Alternatively, where the delivery assist devices comprise a secondary catheter, the atraumatic tip (e.g., a pigtail shaped distal extension) may be coupled to and extend from a distal end of the secondary catheter. In any case, the secondary catheter may be referred to as a "pigtail catheter". In some aspects, the delivery assist device may have an outer diameter of 9 Fr. In other aspects, the delivery assist device may have an outer diameter of less than 9 Fr, preferably, 7 Fr.

When pump 1 is inserted into the patient and positioned in the desired position to provide support, e.g., within the left ventricle 2 and aorta, as shown in FIG. 1, motor 8 may be controlled by a control unit 50 to selectively drive rotation of drive shaft 12 and rotor 10 to cause blood from left ventricle 2 to be drawn into pump 1 through inlet 6 and to be expelled from pump 1 through outlet 7. It is to be appreciated that rotor 10 may be rotated by motor 8 in the reverse direction to convey blood in an opposite direction from opening(s) 7 to opening(s) 6. In any case, a user may control operation of motor 8 and other aspects of pump 1 via user input to control unit 50. In some embodiments, control unit 50 may include a control element configured to receive user input. For example, the control element may be a push button, a dial, a user interface displayed on the control unit, or any other suitable control element. Moreover, control unit 50 may include one or more algorithms for automatically controlling operation of motor 8. Control unit 50 may be configured to display operation data associated with the blood pump 1 (e.g., motor speed), the patient (e.g., blood flow rate, pressure, heart signal, etc.), or other relevant data and settings. Control unit 50 may be configured to output notifications (e.g., displayed notifications and/or sounds) to alert the user(s) when operational data values fall beyond predetermined values or ranges, for example if a leak or loss of suction is detected, or when other conditions are detected. The control unit 50 may be operably coupled to the motor 8 via any suitable means. For example, the control unit 50 may be operably coupled to the motor 8 via a driveshaft. In other embodiments, the control unit 50 may be operably coupled to the motor 8 via an electrical connection.

The intravascular blood pump 1 described herein may be used to administer therapy to a patient in accordance with some aspects of the present disclosure. Such therapy includes, for example, support during a high-risk PCI. For example, the blood pump 1 described herein may be intended for temporary ventricular support during elective or urgent high-risk PCI performed in hemodynamically stable patients.

One aspect of the present disclosure provides a method of providing ventricular support for a predetermined patient population during a high-risk percutaneous coronary intervention procedure, the method includes: identifying human patients in the predetermined patient population as meeting at least one or more eligibility criteria; inserting a delivery assist device into a vasculature of each of the identified human patients; inserting a mechanical circulatory support device into the vasculature of each of the identified human patients; delivering, with the aid of the delivery assist device, the mechanical circulatory support device into a heart of each of the identified human patients; operating the mechanical circulatory support device for a support period of 6 hours or less; and identifying a rate of major adverse cardiovascular and cerebrovascular event (MACCE) for the predetermined patient population during an assessment period from the insertion of the mechanical circulatory support device into the vasculature of each of the identified human patients through about 30 days after the high-risk percutaneous coronary intervention procedure. In one aspect, the at least one or more eligibility criteria comprises a hemodynamically stable human patient. The rate of MACCE may be about 6.3%.

The high-risk PCI may be an elective or urgent high-risk PCI. In some embodiments, the high-risk PCI may not be an emergent high-risk PCI.

The predetermined patient population includes human patients identified as meeting at least one or more eligibility criteria, such as, being a hemodynamically stable human patient. In some embodiments, the at least one or more eligibility criteria may further include an age of each of the identified human patients being from 18 years through 90 years. In some embodiments, the at least one or more eligibility criteria may further include an assessment that the high-risk PCI procedure is a therapeutic option for each of the identified human patients. Typically, a heart team, including a cardiac surgeon, may make such a determination about the high-risk PCI is an appropriate therapeutic option. In some embodiments, the at least one or more eligibility criteria may further comprise a written informed consent from the human patient.

In some embodiments, the at least one or more eligibility criteria may further comprise not meeting or being outside or lacking symptoms of certain exclusion criteria. Non-limiting examples of exclusion criteria may include, for example, aortic valve disease that is anticipated to be prohibitive to the mechanical circulatory support device crossing, including greater than mild aortic stenosis; previous aortic valve replacement or reconstruction; thrombus in left ventricle; the human patient with known aortic vessel disease or with aortic dissection; any contraindication that precludes placing the mechanical circulatory support device including aortic, iliac or femoral disease such as tortuosity, extensive atherosclerotic disease or stenosis; prior stroke with any permanent, significant (mRS>2) neurologic deficit or any prior intracranial hemorrhage or any prior subdural hematoma or known intracranial pathology pre-disposing to intracranial bleeding, such as an arteriovenous malformation or mass; cardiogenic shock or acutely decompensated pre-existing chronic heart failure (cardiogenic shock is defined as: systemic hypotension (systolic blood pressure (BP)<90 mmHg or the need for inotropes/pressors to maintain a systolic BP>90 mmHg) plus one of the following: any requirement for pressors/inotropes prior to arrival at the catheterization laboratory, clinical evidence of end-organ hypoperfusion or use of IABP or any other circulatory support device); infection of the proposed procedural access site or suspected systemic active infection, including any fever; the human patient may have been previously been symptomatic with or hospitalized for COVID-19 unless he/she may have been discharged (if hospitalized) and may have been asymptomatic for ≥8 weeks; known contraindication to heparin (i.e., heparin-induced thrombocytopenia), contrast media or Study-required medication(s) (i.e., aspirin); platelet count <75 k, bleeding diathesis, coagulopathy or unwilling to receive blood transfusions; human patient may be on dialysis; human patient may be suspected or known to be pregnant; the human patient may have other medical, social or psychological problems that, in the opinion of the investigator, may compromise the human patient's ability to give written informed consent and/or to comply with study procedures; participation in the active treatment or follow-up phase of another clinical study of an investigational drug or device which may not have reached its primary endpoint; or the human patient may belong to a vulnerable population.

Non-limiting examples of the vulnerable population may include, for example, individuals with mental disability, persons in nursing homes, children, impoverished persons, homeless persons, nomads, refugees or those permanently incapable of giving informed consent. In some embodiments, vulnerable population may also include members of a group with a hierarchical structure such as university students, subordinate hospital and laboratory personnel, employees of the sponsor of the study, members of the armed forces or persons kept in detention.

In some embodiments, the at least one or more eligibility criteria may not exclude human patients with mild aortic stenosis. However, the at least one or more eligibility criteria may exclude human patients with greater than mild aortic stenosis that was anticipated to be prohibitive to the mechanical circulatory support device crossing their aortic valves.

In some embodiments, the delivery assist device is a catheter, a wire, or a steerable catheter. In some embodiments, the delivery assist device includes an atraumatic tip. The atraumatic tip may be coupled to a distal end of the delivery assist device.

In some embodiments, inserting the mechanical circulatory support device into the vasculature of each of the identified human patients includes inserting an introducer sheath into the vasculature of each of the identified human patients and advancing the mechanical circulatory support device through the introducer sheath.

In some embodiments, delivering, with the aid of the delivery assist device, the mechanical circulatory support device into the heart of each of the identified human patients will require the mechanical circulatory support device to cross an aortic valve of each of the heart of the identified human patients in the presence of the delivery assist device.

In some embodiments, the delivery assist device may be configured to hold open an aortic valve leaflet as the mechanical circulatory support device crosses the aortic valve of each of the heart of the identified human patients.

In some embodiments, the delivery assist device may be a secondary or companion catheter that is separate from a catheter connected to a proximal end of the mechanical circulatory support device. In some embodiments, a distal end of the secondary or companion catheter may be formed as an atraumatic tip having a predetermined shape and stiffness to aid delivery and positioning of the mechanical circulatory support device. In some embodiments, the delivery assist device may be one or more of a wire adjacent the mechanical circulatory support device when the delivery assist device and the mechanical circulatory support device are inserted into the vasculature of each of the identified human patients.

The mechanical circulatory support device of the present disclosure may provide temporary support to each of the identified human patients during the high-risk PCI. In some embodiments, the mechanical circulatory support device may be operated for a support period of 6 hours or less. In some embodiments, the mechanical circulatory support device may be operated for a support period of 30 minutes, 1 hour, 1.5 hours, 2 hours, 2.5 hours, 3 hours, 3.5 hours, 4 hours, 4.5 hours, 5 hours, 5.5 hours, or 6 hours.

In some embodiments, the assessment period may be from the insertion of the mechanical circulatory support device into the vasculature of each of the identified human patients through 25 days after the high-risk percutaneous coronary intervention procedure. In some embodiments, the assessment period may be from the insertion of the mechanical circulatory support device into the vasculature of each of the identified human patients through 35 days after the high-risk percutaneous coronary intervention procedure.

In some embodiments, the assessment period may be from the insertion of the introducer sheath into the vasculature of each of the identified human patients through about 30 days after the high-risk percutaneous coronary intervention procedure. In some embodiments, the assessment period may be from the insertion of the introducer sheath into the vasculature of each of the identified human patients through about 25 days after the high-risk percutaneous coronary intervention procedure. In some embodiments, the assessment period may be from the insertion of the introducer sheath into the vasculature of each of the identified human patients through about 35 days after the high-risk percutaneous coronary intervention procedure.

In some embodiments, the mechanical circulatory support device may be a blood pump comprising: a catheter; a housing in which a rotor is housed, the housing being attached to a distal end of the catheter; and a drive shaft extending through the catheter and connected to the rotor and a motor.

In some embodiments, the mechanical circulatory support device may be expandable. In some embodiments, the housing, the rotor, or both the housing and the rotor of the blood pump may be able to be deformed reversibly elastically in a radial direction between a first radially compressed state and a second radially expanded state.

In some embodiments, the housing of the blood pump in the first radially compressed state may have a diameter of about 9 Fr.

In some embodiments, the blood pump may be configured to provide a blood flow rate of about 5 liters per minute.

In some embodiments, the motor may be located outside the body of each of the identified human patients.

In some embodiments, the rate of MACCE may be from about 5.9% to about 12.9%. In some embodiments, the rate of MACCE may be below 24.4%.

Another aspect of the present disclosure provides a system or a mechanical circulatory support device for providing a rate of incidence of MACCE of about 6.3% for the predetermined patient population during the assessment period of the high-risk percutaneous coronary intervention procedure using the method described above.

Yet another aspect of the present disclosure provides a method of providing ventricular support for a predetermined patient population during a high-risk percutaneous coronary intervention procedure, the method includes: identifying human patients in the predetermined patient population as meeting at least one or more eligibility criteria; inserting a delivery assist device into a vasculature of each of the identified human patients; inserting a mechanical circulatory support device into the vasculature of each of the identified human patients; delivering, with the aid of the delivery assist device, the mechanical circulatory support device into a heart of each of the identified human patients; operating the mechanical circulatory support device for a support period of less than 6 hours; and identifying a rate of incidence of ventricular arrhythmia for the predetermined patient population during the high-risk PCI procedure. The at least one or more eligibility criteria comprises a hemodynamically stable human patient.

In some embodiments, the ventricular arrhythmia includes ectopy and bigeminy.

Yet another aspect of the present disclosure provides a method of providing ventricular support for a human patient during a high-risk PCI procedure, the method includes: identifying the human patient as meeting at least one or more eligibility criteria; inserting a delivery assist device into a vasculature of the identified human patient; inserting a mechanical circulatory support device into the vasculature of the identified human patient; delivering, with the aid of the delivery assist device, the mechanical circulatory support device into a heart of the identified human patient; operating the mechanical circulatory support device for a support period of less than 6 hours; and identifying, with the aid of a patient console, diagnosing a ventricular arrhythmia in the identified human patient during the high-risk percutaneous coronary intervention procedure, wherein the at least one or more eligibility criteria comprises a hemodynamically stable human patient.

In some embodiments, the one or more eligibility criteria may include hemodynamically stable human patients with severe coronary artery disease.

In some embodiments, the at least one or more eligibility criteria may further include an assessment that the high-risk percutaneous coronary intervention procedure is a therapeutic option for each of the identified human patients.

In some embodiments, the mechanical circulatory support device may prevent hemodynamic instability, the hemodynamic instability resulting from repeat episodes of reversible myocardial ischemia occurring during a planned temporary coronary occlusion.

In some embodiments, the mechanical circulatory support device may reduce a peri-procedural adverse event.

In some embodiments, the mechanical circulatory support device may reduce a post-procedural adverse event.

In some embodiments, the step of inserting the mechanical circulatory support device into the vasculature of each of the identified human patients may include inserting a delivery assist device into a vasculature of each of the identified human patients.

In some embodiments, the delivery assist device may be a catheter, a guidewire, or a steerable catheter.

In some embodiments, the delivery assist device may include an atraumatic tip. The atraumatic tip may be coupled to a distal end of the delivery assist device.

In some embodiments, the high-risk percutaneous coronary intervention may be an elective procedure.

In some embodiments, the high-risk percutaneous coronary intervention may be an urgent procedure.

In some embodiments, an insertion size of the mechanical circulatory support device may have a cross-sectional diameter between about 8 Fr and about 13 Fr.

In some embodiments, the insertion size may have a cross-sectional diameter between about 9 Fr and about 12 Fr.

In some embodiments, the insertion size may have a cross-sectional diameter between about 10 Fr and about 11 Fr.

In some embodiments, the mechanical circulatory support device may have a compressed state and an expanded state.

In some embodiments, the expanded state may have a cross-sectional diameter between about 15 Fr and about 30 Fr.

In some embodiments, the expanded state may have a cross-sectional diameter between about 15 Fr and about 25 Fr.

In some embodiments, the expanded state may have a cross-sectional diameter between about 15 Fr and about 20 Fr.

In some embodiments, the expanded state may have a cross-sectional diameter of 18 Fr.

In some embodiments, the step of delivering the mechanical circulatory support device into a heart of each of the identified human patients may include the step of advancing the mechanical circulatory support device over a guidewire.

In some embodiments, the support period may be less than 6 hours.

In some embodiments, delivering, with the aid of the delivery assist device, the mechanical circulatory support device into the heart of each of the identified human patients includes the mechanical circulatory support device crossing an aortic valve of each of the heart of the identified human patients in the presence of the delivery assist device.

Yet another aspect of the present disclosure provides a method of providing ventricular support during a high-risk percutaneous coronary intervention in a predetermined patient population of hemodynamically stable patients with severe coronary artery disease, the method includes: identifying human patients in the predetermined patient population as meeting at least one or more eligibility criteria; inserting a mechanical circulatory support device into the vasculature of each of the identified human patients; delivering the mechanical circulatory support device into a heart of each of the identified human patients; and operating the mechanical circulatory support device for a support period of up to 6 hours; wherein the mechanical circulatory support device is an Impella ECP™ device.

In some embodiments, the at least one or more eligibility criteria may include an assessment that the high-risk percutaneous coronary intervention procedure is a therapeutic option for each of the identified human patients.

Yet another aspect of the present disclosure provides a method of preventing hemodynamic instability resulting from repeat episodes of reversible myocardial ischemia occurring during a planned temporary coronary occlusion, the method includes: identifying human patients in the predetermined patient population as meeting at least one or more eligibility criteria; inserting a mechanical circulatory support device into the vasculature of each of the identified human patients; delivering the mechanical circulatory support device into a heart of each of the identified human patients; and operating the mechanical circulatory support device for a support period of less than 6 hours; wherein the at least one or more eligibility criteria comprises a hemodynamically stable human patient; and wherein the mechanical circulatory support device is an Impella ECP™ device.

Another aspect of the present disclosure provides a method of providing ventricular support for a human patient during a high-risk percutaneous coronary intervention procedure, the method comprising: inserting a mechanical circulatory support device into the vasculature of a human patient, the mechanical circulatory support device being movable between a compressed state and an expanded state; delivering, with the aid of a delivery assist device, the mechanical circulatory support device into a heart of the human patient; operating the mechanical circulatory support device for a support period; and wherein a clinically significant arrhythmia adverse event (AE) associated with the mechanical circulatory support device experiencing the arrhythmia event between the time of vascular access with the mechanical circulatory support device and removal of the mechanical circulatory support device from the vasculature is approximately 2.3%.

EXAMPLES

The present disclosure may be better understood by reference to the following non-limiting examples, which are exemplary of the disclosure. They should in no way be construed, however, as limiting the breath of the scope of the disclosure.

Eligibility Criteria: Inclusion and Exclusion Criteria

Eligibility-Inclusion Criteria: Participating patient population was identified as meeting the following criteria: Age ≥18 years and ≤90 years; signed an informed consent; is a hemodynamically stable human patient, and a heart team, including a cardiac surgeon, has determined that an elective or urgent (not emergent) high-risk PCI is an appropriate therapeutic option.

Eligibility-Exclusion Criteria: Participating patient population was identified as also not meeting any of the following criteria: aortic valve disease that is anticipated to be prohibitive to Impella ECP™ crossing, including greater than mild aortic stenosis; previous aortic valve replacement or reconstruction; thrombus in left ventricle; subjects with known aortic vessel disease or with aortic dissection; any contraindication that precludes placing the Impella ECP™ including aortic, iliac or femoral disease such as tortuosity, extensive atherosclerotic disease or stenosis; prior stroke with any permanent, significant (mRS>2) neurologic deficit or any prior intracranial hemorrhage or any prior subdural hematoma or known intracranial pathology pre-disposing to intracranial bleeding, such as an arteriovenous malformation or mass; cardiogenic shock or acutely decompensated pre-existing chronic heart failure (cardiogenic shock is defined as: systemic hypotension (systolic blood pressure (BP) <90 mmHg or the need for inotropes/pressors to maintain a systolic BP>90 mmHg) plus one of the following: any requirement for pressors/inotropes prior to arrival at the catheterization laboratory, clinical evidence of end-organ hypoperfusion or use of IABP or any other circulatory support device); infection of the proposed procedural access site or suspected systemic active infection, including any fever; subject has previously been symptomatic with or hospitalized for COVID-19 unless he/she has been discharged (if hospitalized) and asymptomatic for ≥8 weeks; known contraindication to heparin (i.e., heparin-induced thrombocytopenia), contrast media or Study-required medication(s) (i.e., aspirin); platelet count <75 k, bleeding diathesis, coagulopathy or unwilling to receive blood transfusions; subject is on dialysis; participant is suspected or known to be pregnant; subject has other medical, social or psychological problems that, in the opinion of the investigator, compromises the subject's ability to give written informed consent and/or to comply with study procedures; participation in the active treatment or follow-up phase of another clinical study of an investigational drug or device which has not reached its primary endpoint; or subject belongs to a vulnerable population.

Vulnerable subject populations were defined as individuals with mental disability, persons in nursing homes, children, impoverished persons, homeless persons, nomads, refugees or those permanently incapable of giving informed consent. Vulnerable populations may also have included members of a group with a hierarchical structure such as university students, subordinate hospital and laboratory personnel, employees of the sponsor of the study, members of the armed forces or persons kept in detention.

Study Participants

The study population was human patients undergoing elective or urgent high-risk PCI procedures. All subjects receiving hemodynamic-supported high-risk PCI at participating sites were screened for eligibility. Following informed consent, subjects eligible for a high-risk PCI procedure that met all of the inclusion and none of the exclusion criteria were enrolled into the study.

Three hundred and twenty-two subjects were screened for enrollment by 18 enrolling pivotal study sites in the Impella ECP™ pivotal study. Of those screened, 66 subjects did not meet all study criteria. Thus, a total of 256 subjects were enrolled in the study, all of which were included in the Full Analysis Set (FAS). For purposes herein, FAS included all subjects enrolled and treated with Impella ECP™ or attempted treatment with Impella ECP™. The primary analysis for baseline variables, and the primary endpoint, and the secondary endpoints, as well as safety endpoints were conducted on the FAS.

A summary of the baseline medical history of the patient population is shown in Table 1. The subjects were, on average, 72 years old. The medical history of the subjects highlights many of the expected risk factors and co-morbidities associated with heart disease. For example, 56% of subjects were diabetic, 94% were hypertensive, 95% had dyslipidemia/hyperlipidemia, 32% had renal insufficiency or renal failure, and 58% had smoked tobacco, with 22% currently smoking tobacco. Prior to treatment with Impella ECP™, the average baseline ejection fraction (EF) was 47% among the subjects. Additionally, 18% of subjects had peripheral vascular disease and 50% had a prior myocardial infarction. The average body mass index (BMI) of the subjects was 29.2 kg/m². Also, 7.42% of the subjects had valve stenosis, of which 63.16% had aortic valve stenosis.

TABLE 1

| Characteristics | Full Analysis Set (N = 256) | |
|---|---|---|
| Alcohol Use | | |
| Yes | 40.63% | (104/256) |
| No | 57.42% | (147/256) |
| Unknown | 1.95% | (5/256) |
| Smoking Tobacco | | |
| Yes | 58.20% | (149/256) |
| Current | 22.15% | (33/149) |
| Former (quit within prior 12 months) | 8.72% | (13/149) |
| Former (quit greater than 12 months) | 69.13% | (103/149) |
| Unknown/Not Reported | 0% | (0/149) |
| No | 40.23% | (103/256) |
| Unknown | 1.56% | (4/256) |
| Diabetes Mellitus | | |
| Yes | 55.86% | (143/256) |
| Type | | |
| I | 1.40% | (2/143) |
| II | 98.60% | (141/143) |
| Unknown | 0% | (0/143) |
| Treatment | | |
| None | 2.10% | (3/143) |
| Oral | 43.36% | (62/143) |
| Insulin | 27.27% | (39/143) |
| Oral/Insulin | 25.87% | (37/143) |
| Diet | 1.40% | (2/143) |

TABLE 1-continued

| Characteristics | Full Analysis Set (N = 256) | |
|---|---|---|
| Unknown | 0% | (0/143) |
| No | 44.14% | (113/256) |
| Unknown | 0% | (0/256) |
| Renal Insufficiency or Failure | | |
| Yes | 32.03% | (82/256) |
| No | 67.97% | (174/256) |
| Unknown | 0% | (0/256) |
| Anemia | | |
| Yes | 28.52% | (73/256) |
| No | 71.48% | (183/256) |
| Unknown | 0% | (0/256) |
| Chronic Obstructive Pulmonary Disease (COPD) | | |
| Yes | 20.70% | (53/256) |
| No | 78.91% | (202/256) |
| Unknown | 0.39% | (1/256) |
| Hepatitis | | |
| Yes | 1.56% | (4/256) |
| No | 97.27% | (249/256) |
| Unknown | 1.17% | (3/256) |
| Coagulopathy (clotting or bleeding disorder) | | |
| Yes | 0.39% | (1/256) |
| No | 98.44% | (252/256) |
| Unknown | 1.17% | (3/256) |
| Hemophilia | | |
| Yes | 0% | (0/256) |
| No | 100% | (256/256) |
| Unknown | 0% | (0/256) |
| Heparin-Induced Thrombocytopenia (HIT) | | |
| Yes | 0% | (0/256) |
| No | 100% | (256/256) |
| Unknown | 0% | (0/256) |
| Idiopathic Thrombocytopenia Purpura | | |
| Yes | 0.39% | (1/256) |
| No | 99.22% | (254/256) |
| Unknown | 0.39% | (1/256) |
| Polycythemia Vera | | |
| Yes | 0% | (0/256) |
| No | 99.61% | (255/256) |
| Unknown | 0.39% | (1/256) |
| Uncorrectable Bleeding Diathesis | | |
| Yes | 0% | (0/256) |
| No | 100% | (256/256) |
| Unknown | 0% | (0/256) |
| Platelet Dysfunction | | |
| Yes | 1.17% | (3/256) |
| No | 98.83% | (253/256) |
| Unknown | 0% | (0/256) |
| COVID19 Diagnosis | | |
| Yes | 10.94% | (28/256) |
| No | 84.38% | (216/256) |
| Unknown | 4.69% | (12/256) |
| Dyslipidemia/Hyperlipidemia | | |
| Yes | 94.53% | (242/256) |
| Currently Taking Medication | | |
| Yes | 95.04% | (230/242) |
| No | 4.96% | (12/242) |
| Unknown | 0% | (0/242) |
| No | 5.47% | (14/256) |
| Unknown | 0% | (0/256) |

TABLE 1-continued

| Characteristics | Full Analysis Set (N = 256) |
|---|---|
| Hypertension | |
| Yes | 93.75% (240/256) |
| Currently Taking Medication | |
| Yes | 94.17% (226/240) |
| No | 5.42% (13/240) |
| Unknown | 0.42% (1/240) |
| No | 6.25% (16/256) |
| Unknown | 0% (0/256) |
| Subject is currently on injection or infusion of thrombolytic agent | |
| Yes | 2.73% (7/256) |
| No | 97.27% (249/256) |
| Unknown | 0% (0/256) |
| Coronary Artery Disease (CAD) | |
| Yes | 96.88% (248/256) |
| No | 3.13% (8/256) |
| Unknown | 0% (0/256) |
| Myocardial Infarction (MI) | |
| Yes | 50.00% (128/256) |
| No | 48.83% (125/256) |
| Unknown | 1.17% (3/256) |
| Unstable Angina Pectoris | |
| Yes | 30.47% (78/256) |
| No | 64.45% (165/256) |
| Unknown | 5.08% (13/256) |
| Previous Percutaneous Coronary Intervention (PCI) | |
| Yes | 43.36% (111/256) |
| No | 56.64% (145/256) |
| Unknown | 0% (0/256) |
| Prior Coronary Artery Bypass Graft (CABG) | |
| Yes | 14.06% (36/256) |
| No | 85.94% (220/256) |
| Unknown | 0% (0/256) |
| Other Previous Cardiac Surgery | |
| Yes | 6.25% (16/256) |
| No | 93.36% (239/256) |
| Unknown | 0.39% (1/256) |
| Transient Ischemic Attack (TIA) | |
| Yes | 5.47% (14/256) |
| No | 93.75% (240/256) |
| Unknown | 0.78% (2/256) |
| Peripheral Vascular Disease (PVD) | |
| Yes | 17.97% (46/256) |
| No | 80.86% (207/256) |
| Unknown | 1.17% (3/256) |
| Intracranial Aneurysm or Bleeding | |
| Yes | 1.56% (4/256) |
| No | 98.05% (251/256) |
| Unknown | 0.39% (1/256) |
| Stroke | |
| Yes | 7.81% (20/256) |
| Type | |
| Ischemic | 55.00% (11/20) |
| Hemorrhagic | 5.00% (1/20) |
| Unknown | 40.00% (8/20) |
| No | 91.80% (235/256) |
| Unknown | 0.39% (1/256) |
| Heart Failure | |
| Yes | 55.47% (142/256) |
| HF with preserved EF | 25.35% (36/142) |

TABLE 1-continued

| Characteristics | Full Analysis Set (N = 256) |
|---|---|
| HF with reduced EF | 70.42% (100/142) |
| Unknown | 4.23% (6/142) |
| No | 43.36% (111/256) |
| Unknown | 1.17% (3/256) |
| New York Heart Association (NYHA) Classification | |
| Class I | 5.47% (14/256) |
| Class II | 30.47% (78/256) |
| Class III | 25.78% (66/256) |
| Class IV | 1.95% (5/256) |
| Unknown | 36.33% (93/256) |
| Dyspnea | |
| Yes | 60.94% (156/256) |
| No | 38.67% (99/256) |
| Unknown | 0.39% (1/256) |
| Fatigue | |
| Yes | 36.72% (94/256) |
| No | 59.77% (153/256) |
| Unknown | 3.52% (9/256) |
| Valve Regurgitation | |
| Present | 79.69% (204/256) |
| Location | |
| Mitral | 86.76% (177/204) |
| Tricuspid | 78.43% (160/204) |
| Aortic | 42.65% (87/204) |
| Pulmonary | 47.06% (96/204) |
| Absent | 19.53% (50/256) |
| Unknown | 0.78% (2/256) |
| Valve Stenosis | |
| Present | 7.42% (19/256) |
| Location | |
| Mitral | 31.58% (6/19) |
| Tricuspid | 0% (0/19) |
| Aortic | 63.16% (12/19) |
| Pulmonary | 5.26% (1/19) |
| Absent | 91.41% (234/256) |
| Unknown | 1.17% (3/256) |
| Valve Mixed Disease | |
| Present | 4.30% (11/256) |
| Location | |
| Mitral | 81.82% (9/11) |
| Tricuspid | 45.45% (5/11) |
| Aortic | 27.27% (3/11) |
| Pulmonary | 0% (0/11) |
| Absent | 90.63% (232/256) |
| Unknown | 5.08% (13/256) |
| Aortic Dissection | |
| Yes | 0% (0/256) |
| No | 99.22% (254/256) |
| Unknown | 0.78% (2/256) |
| Baseline Left Ventricular Ejection Fraction (LVEF) (%) | |
| Mean ± SD (N) | 46.76 ± 15.38 (256) |
| Median (Q1, Q3) | 50.00 (35.00, 60.00) |
| Range (Min, Max) | (13.00, 75.00) |

Method

Figure 4:
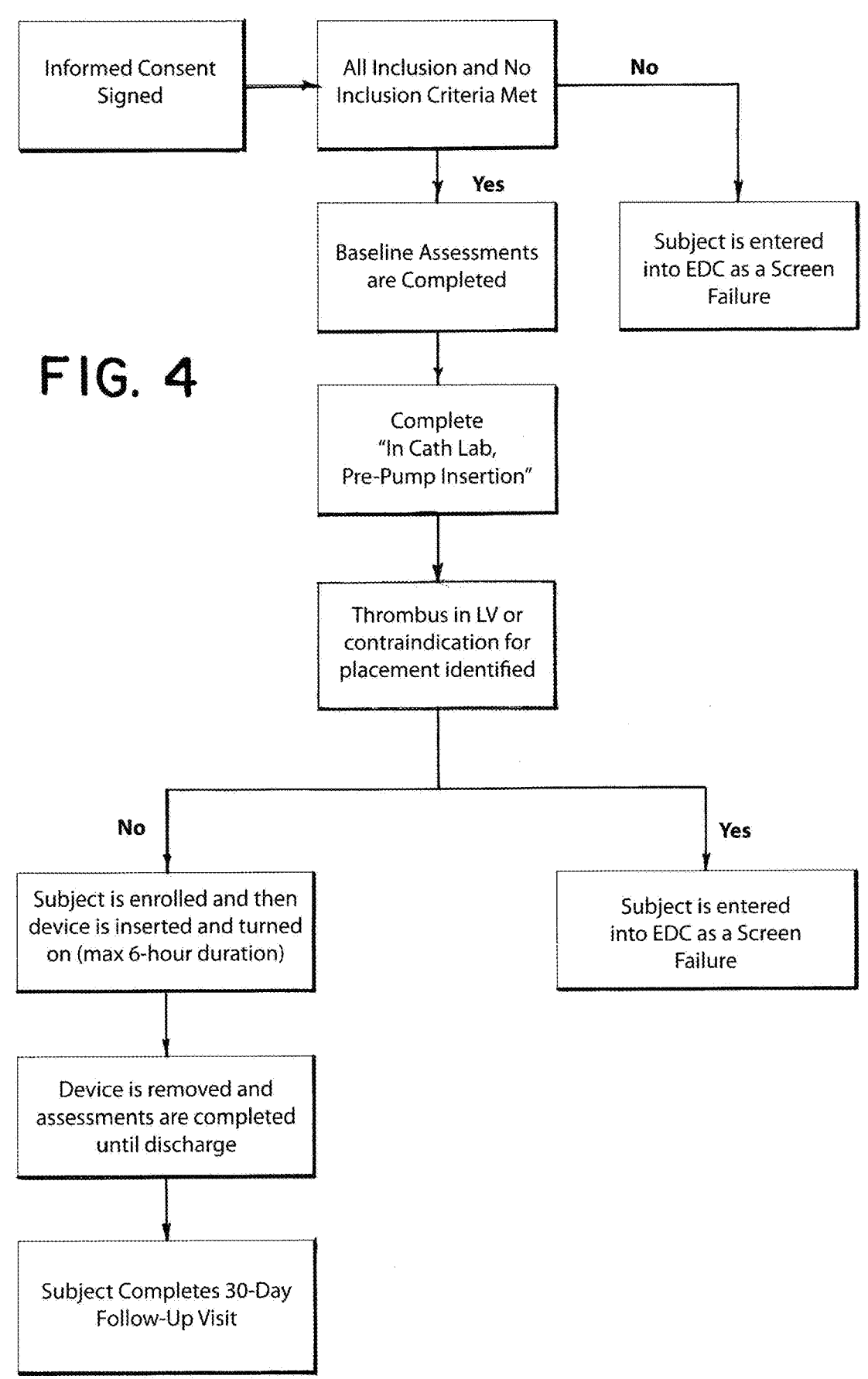
FIG. 4 illustrates a flow design of the study described herein.

Subjects underwent high-risk PCI with Impella ECP™ support. Impella ECP™ was crimped, then it was advanced through a 9 Fr introducer sheath, inserted at the access site, and across the subject's aortic valve and into the left ventricle. The percutaneous insertion of the Impella ECP™ was performed under fluoroscopy. For example, in some instances, a secondary or companion catheter (separate from the catheter of the Impella ECP™) was used as the delivery assist device. In some instances, the secondary or companion catheter had a pigtail at its distal end. In some instances, secondary or companion catheter had a maximum outer diameter of 7 Fr. In some instances, the delivery assist device was inserted together (e.g., in parallel) or separately from the Impella ECP™ through the introducer sheath. In some instances, the delivery assist device was inserted adjacent to the Impella ECP™. In some instances, the Impella ECP™ was not advanced over the delivery assist device. For example, where the delivery assist device was a guidewire, the Impella ECP™ was not advanced over the guidewire. The mean time to cross the aortic valve was 1.30±2.12 minutes for 249 subjects. After successful insertion, the Impella ECP™ was activated to provide the desired level of hemodynamic support prior to initiation of the PCI procedure. The PCI procedure was performed. The Impella ECP™ was in situ for a maximum of 6 hours. The mean Impella ECP™ support duration was 77.2 minutes (SD 35.5). Any adverse events were captured and recorded. Once the PCI procedure was completed, Impella ECP™ was weaned and removed. The access or insertion site was closed with an 8 French or smaller bioabsorbable closure device. The bioabsorbable closure device in some subjects comprises collagen. Subjects were followed up 30 days after the PCI. There was a window of +5 days provided for the 30-day follow-up visit. The study flow diagram is shown in FIG. 4 and a procedure summary is shown in Table 2.

TABLE 2

| Characteristics | Full Analysis Set (N = 256) |
| --- | --- |
| Interventional Procedure | |
| Aspirin was administered prior to the procedure | 99.61% (255/256) |
| If yes, oral antiplatelet therapy with either a minimum dose of aspirin 81 mg daily for at least two (2) days prior to the planned PCI or aspirin 325 mg at least 12 hours prior to the planned PCI | 99.22% (253/255) |
| If yes, other Aspirin dose | 10.59% (27/255) |
| More than one Impella ECP ™ pump used during index procedure | 2.34% (6/256) |
| Total Fluoroscopy time (minutes) | |
| Mean ± SD (N) | 37.47 ± 16.52 (256) |
| Median (Q1, Q3) | 34.50 (25.50, 44.00) |
| Range (Min, Max) | (10.00, 102.00) |
| Total volume of contrast used (ml) | |
| Mean ± SD (N) | 170.37 ± 80.98 (255) |
| Median (Q1, Q3) | 160.00 (115.00, 212.00) |
| Range (Min, Max) | (25.00, 550.00) |
| Impella ECP ™ placement | |
| Total time duration to cross the aortic valve (minutes) | |
| Mean ± SD (N) | 1.30 ± 2.12 (249) |
| Median (Q1, Q3) | 0.67 (0.20, 1.50) |
| Range (Min, Max) | (0.02, 20.00) |
| Total time duration to cross the aortic valve was unknown/not documented | 2.73% (7/256) |
| Buddy wire or other device was used to cross aortic valve | 100% (256/256) |
| Ventricular arrhythmia (including ectopy and bigeminy) occurred during the procedure | 56.64% (145/256) |
| Ventricular arrhythmia (including ectopy and bigeminy) lasted more than 60 seconds | 42.76% (62/145) |
| Impella pump was repositioned due to ventricular arrhythmia (including ectopy and bigeminy) | 33.10% (48/145) |
| Impella pump was removed due to ventricular arrhythmia (including ectopy and bigeminy) | 0.69% (1/145) |
| Side (Which Leg) of Pump Insertion | |
| Left | 70.70% (181/256) |
| Right | 29.30% (75/256) |
| Additional ECP Pump Use Information | |
| This pump was inserted | 66.67% (4/6) |
| This pump crossed the aortic valve | 50.00% (2/4) |
| Buddy wire or other device was used to cross aortic valve | 100% (2/2) |
| This pump was started | 100% (2/2) |
| If this pump was inserted, answer the following for this pump ONLY, from insertion through removal ("procedure"): | |
| Ventricular arrhythmia (including ectopy and bigeminy) occurred during the procedure | 66.67% (2/3) |
| Ventricular arrhythmia (including ectopy and bigeminy) lasted more than 60 seconds | 50.00% (1/2) |

US 12,667,712 B2

23

24

TABLE 2-continued

| Characteristics | Full Analysis Set (N = 256) | |
| --- | --- | --- |
| Impella pump was repositioned due to ventricular arrhythmia (including ectopy and bigeminy) | 100% | (2/2) |
| Impella pump was removed due to ventricular arrhythmia (including ectopy and bigeminy) | 0% | (0/2) |
| Reason for Pump Removal | | |
| Adverse Event | 0% | (0/4) |
| Device Deficiency | 100% | (4/4) |
| Other | 0% | (0/4) |
| There was another pump used that was removed prior to the completion of the HRPCI | 0% | (0/6) |
| Post Removal | | |
| Inotropes/Vasopressors were used at any time during the procedure | 10.94% | (28/256) |
| Blood transfusion was required at any time during the procedure (packed cells, fresh frozen plasma, thrombocytes) | 0.78% | (2/256) |
| Any difficulty with Pump Removal | 1.56% | (4/256) |
| Reason for final Pump Removal | | |
| Planned Removal | 99.22% | (254/256) |
| 6 Hour Maximum Treatment Time Reached | 0% | (0/256) |
| Adverse Event | 0.78% | (2/256) |
| Device Deficiency | 0% | (0/256) |
| Other | 0% | (0/256) |
| Urinalysis was performed post-removal due to clinical suspicion of hemolysis | 1.17% | (3/256) |
| Impella Access Vascular Closure Method and Device | | |
| First Closure Attempt | | |
| Method of Vascular Closure in this attempt | | |
| Pre Closure | 20.70% | (53/256) |
| Post Closure | 78.13% | (200/256) |
| Manual Compression | 1.17% | (3/256) |
| Dry Closure | 0% | (0/256) |
| Other | 0% | (0/256) |
| Vascular Closure device used in this attempt | | |
| Not applicable | 1.17% | (3/256) |
| Angio-Seal 6F | 1.95% | (5/256) |
| Angio-Seal 8F | 69.92% | (179/256) |
| Perclose | 26.95% | (69/256) |
| Mynx | 0% | (0/256) |
| Manta | 0% | (0/256) |
| Other | 0% | (0/256) |
| Second Closure Attempt | | |
| Method of Vascular Closure in this attempt | | |
| Pre Closure | 5.71% | (2/35) |
| Post Closure | 20.00% | (7/35) |
| Manual Compression | 65.71% | (23/35) |
| Dry Closure | 8.57% | (3/35) |
| Other | 0% | (0/35) |
| Vascular Closure device used in this attempt | | |
| Not applicable | 65.71% | (23/35) |
| Angio-Seal 6F | 5.71% | (2/35) |
| Angio-Seal 8F | 8.57% | (3/35) |
| Perclose | 8.57% | (3/35) |
| Mynx | 2.86% | (1/35) |
| Manta | 0% | (0/35) |
| Other | 8.57% | (3/35) |
| Third Closure Attempt | | |
| Method of Vascular Closure in this attempt | | |
| Pre Closure | 22.22% | (2/9) |
| Post Closure | 11.11% | (1/9) |
| Manual Compression | 44.44% | (4/9) |
| Dry Closure | 0% | (0/9) |
| Other | 22.22% | (2/9) |
| Vascular Closure device used in this attempt | | |
| Not applicable | 55.56% | (5/9) |
| Angio-Seal 6F | 0% | (0/9) |
| Angio-Seal 8F | 0% | (0/9) |
| Perclose | 22.22% | (2/9) |

TABLE 2-continued

| Characteristics | Full Analysis Set (N = 256) |
|---|---|
| Mynx | 0% (0/9) |
| Manta | 0% (0/9) |
| Other | 22.22% (2/9) |

Results

Primary Endpoint: Major Adverse Cardiovascular and Cerebrovascular Event (MACCE)

Statistical Analysis Plan-Primary Endpoint (MACCE): The primary endpoint was the rate of MACCE from device delivery through 30 days. MACCE is a composite of death, stroke, myocardial infarction, and target vessel repeat revascularization. Device delivery timepoint was defined to start at the time that the 9 Fr introducer sheath touched the skin of the patient.

The following were the hypotheses for the primary endpoint MACCE:

Null hypothesis $H_0$: $\pi \geq 24.4\%$, vs. Alternative Hypothesis $H_A$: $\pi < 24.4\%$ where $\pi$ was the true 30-day MACCE rate of Impella ECP™ treated patients and 24.4% was the performance goal. The performance goal was determined to be an acceptable outcome in the high-risk PCI population studied and was established using, for example, data from a randomized controlled clinical trial using other hemodynamic support devices and literature review.

Assumptions used in the sample size calculation were the following:

One-sided 5% significant level

90% power

Performance goal of 24.4%

Impella ECP™ true 30-day MACCE rate of 16.3%

A total of 217 evaluable patients yielded 90% power to reject the null hypothesis in favor of the alternative hypothesis. Assuming up to 15% loss to follow-up, 256 patients were enrolled in the study.

Results-Primary Endpoint (MACCE): The overall study composite rate of MACCE events for the subjects through 30 days was 6.3% (15/238). Four subjects had more than one MACCE event. A total of 8 subjects died, 4 had myocardial infarctions, 5 had strokes and 2 had target vessel repeat revascularization. The primary endpoint MACCE results are shown in Table 3.

TABLE 3

| Primary Endpoint | Full Analysis Set (N = 256) |
|---|---|
| MACCE (evaluable)[1] | 6.30% (15/238[2]) |
| Death | 3.36% (8/238) |
| Stroke | 2.10% (5/238) |
| Myocardial Infarction | 1.68% (4/238) |
| Target Vessel Repeat Revascularization | 0.84% (2/238) |

[1]MACCE is the composite of death, stroke, myocardial infarction, and target vessel repeat revascularization.
[2]Denominators indicate the number of subjects with at least 25 days of follow-up, or any MACCE through 30 days post device delivery.

The sub-groups pre-specified in the Statistical Analysis Plan for analysis of the primary endpoint were: Sex (male versus female), race (white versus non-white), and learning curve (first 3 subjects per site versus subsequent subjects). The primary endpoint was consistent across all the pre-specified sub-groups in the study population.

To assess the impact of missing data to study outcome, sensitivity analysis on the primary endpoint exploring the best- and worst-case scenarios as well as multiple imputation were conducted. The MACCE event rate varied from 5.9% to 12.9% in the best- and worst-case scenarios with the multiple imputation estimated MACCE rate being 6.33%. In all scenarios event rates and the corresponding upper bounds of the 95% confidence intervals were below the 24.4% performance goal, as seen in Table 4.

TABLE 4

| Primary Endpoint | Full Analysis Set (N = 256) | Upper Bound of One-sided 95% CI | Performance Goal | P-value |
|---|---|---|---|---|
| MACCE (evaluable) | 6.30% (15/238) | 9.54% | 24.40% | <.0001 |
| MACCE (a first case scenario) | 5.86% (15/256) | 8.88% | 24.40% | <.0001 |
| MACCE (a second case scenario) | 12.89% (33/256) | 16.86% | 24.40% | <.0001 |
| MACCE (tipping point) | 19.92% (51/256) | 24.48% | 24.40% | 0.0529 |
| MACCE (multiple imputation | 6.33% | 8.97% | 24.40% | <.0001 |

As noted above, the rate of MACCE, the primary endpoint, was 6.3% (15/238) with an upper bound of the one-sided 95% confidence interval of 9.5%. This met the performance goal of 24.4% which was established with the assumption of an expected 30-day MACCE rate of 16.3%. Sensitivity analyses resulted in a best-case rate of 15/256 or 5.9% (8.9% upper bound of the CI) and a worst-case rate of 33/256 or 12.9% (16.9% upper bound of the CI). Multiple imputation resulted in a MACCE rate of 6.3% (9.0% upper bound of the CI). In all scenarios the primary endpoint performance goal was met.

Safety Endpoints

Statistical Analysis Plan-Safety Endpoints: The two safety endpoints specified were:

Impella ECP™-related Major Vascular Complications [Time Frame: Device Delivery Through Discharge from the Index Hospital Admission]

Impella ECP™-related Major Bleeding [Time Frame: Device Delivery Through Discharge from the Index Hospital Admission]

Results-Safety Endpoints: The rate of Impella ECP™-related major vascular complications was 1.6%. The rate of Impella ECP™-related major bleeding endpoints was 5.9%. Fifty bleeding events occurred across 22 subjects. Bleeding in Academic Research Consortium (BARC) bleeding of level 3 or greater was observed in 30 of those 50 bleeding events. 15/30 of these events were Impella ECP™-related. Eleven major vascular complications were observed in 9 subjects. Four of these 11 events were related to the device or device procedure, and 7 remaining events were not related to the device or device procedure. A summary of Impella ECP™ safety endpoints is shown in Table 5.

TABLE 5

| Safety Endpoints | Full Analysis Set (N = 256) | [Two-sided 95% CI] |
|---|---|---|
| Impella ECP ™-related Major Vascular Complications (Device Delivery through Discharge from the Index Hospital Admission) | 1.56% (4/256) | [0.43%, 3.95%] |
| Impella ECP ™-related Major Bleeding (Device Delivery through Discharge from the Index Hospital Admission) | 5.86% (15/256) | [3.32%, 9.48%] |

Secondary Endpoints:

Statistical Analysis Plan-Secondary Endpoints: The secondary endpoints specified were:

Major Hemolysis [Time Frame: Device Delivery Through Discharge]

Aortic Valve Injury [Time Frame: Device Delivery Through Discharge]

Escalation of care to Impella CPR [Time Frame: Device Removal through Discharge]

Length of Hospital Stay [Time Frame: Admission Through Discharge]

Results-Secondary Endpoints: Neither major hemolysis nor aortic valve injury occurred in any subjects. Two subjects (0.8%) required escalation from Impella ECP™ to Impella CP. The mean length of stay from admission through discharge was 3.5 days. A summary of Impella ECP™ secondary endpoints is shown in Table 6.

TABLE 6

| Secondary Endpoints | Full Analysis Set (N = 256) |
|---|---|
| Major Hemolysis (Device Delivery through Discharge) | 0% (0/256) |
| Aortic Valve Injury (Device Delivery through Discharge) | 0% (0/256) |
| Escalation of Care to Impella CP (Device Removal through Discharge) | 0.78% (2/256) |
| Length of Hospital Stay (Admission Through Discharge), Days | |
| Mean ± SD (N) | 3.54 ± 4.09 (256) |
| Median (Q1, Q3) | 1.00 (1.00, 5.00) |
| Range (Min, Max) | (0.00, 24.00) |

Other Adverse Events

Some degree of ventricular arrhythmia was reported as occurring during the procedure in 145 of the 256 subjects.

Of those, 62 reported arrhythmias lasting greater than 60 seconds and 31 required repositioning of the device, one of whom required removal of the Impella ECP™. The reported ventricular arrhythmias included ectopy and bigeminy. There were 83 subjects with ventricular arrhythmias that did not last longer than 60 seconds, and 17 of those 83 required repositioning with none requiring removal.

Figure 5:
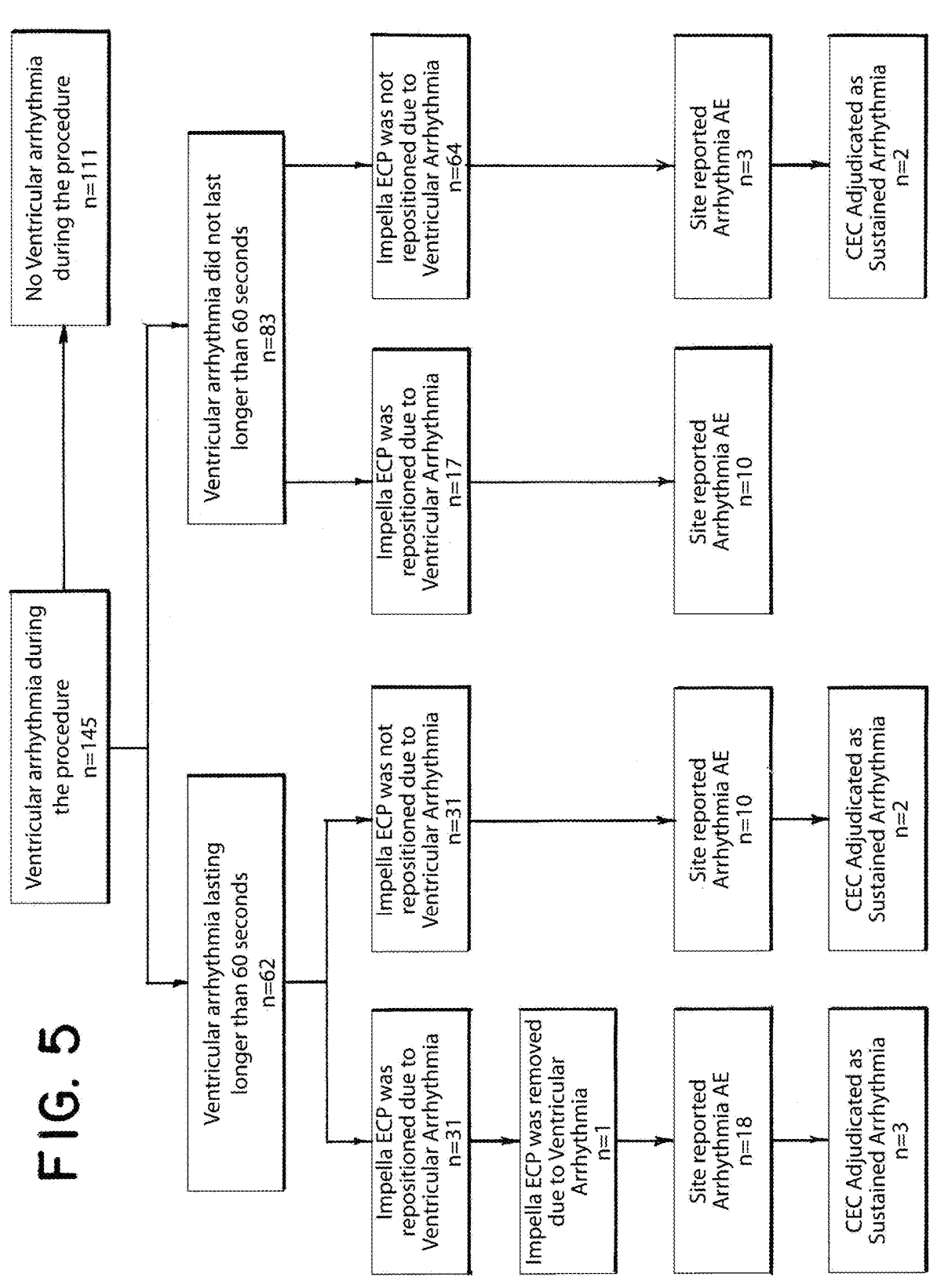
FIG. 5 illustrates a flowchart of the study's site-reported ventricular arrhythmia adverse events.

While ventricular arrhythmias were seen in this study, the majority did not warrant any intervention. As seen in FIG. 5, 41 of the reported observations of ventricular arrhythmia were reported as adverse events. However, only 7 events were adjudicated as sustained arrhythmia. Sustained arrhythmia was defined as ventricular fibrillation, ventricular tachycardia, higher degree conductive disorder or newly developed atrial fibrillation lasting >60 seconds and requiring cardioversion/defibrillation and/or IV amiodarone, during placement of, support with, or removal of the device.

Referring now to FIGS. 6 and 7, the table lists events by both subject and total number of events. Note that a subject can be represented in this table more than once if they had multiple events. Also, note that in row I, repositioning refers to repositioning of the Impella ECP™ pump device.

The majority of all investigated events occurred between the time of vascular access and PCI initiation. Five subjects met the definition of a sustained arrhythmia or had hemodynamic compromise defined as need for inotropic support. However, these events occurred between PCI initiation and device removal in only two of those subjects. While four subjects required pump replacement, none of those replacements occurred between PCI initiation and device removal.

To examine how often support was paused due to an arrhythmia event the Impella ECP™ Pump log files were reviewed for support interruptions of greater than 30 seconds. Five subjects had support interruptions of greater than 30 seconds (Table 2 of Appendix D).

A further analysis was conducted on arrhythmia AEs alone and interventions required as a result of these AEs. Specifically, those subjects with arrhythmia AEs from vascular access through device removal and any one of the following:

Arrhythmia AE requiring repositioning during the PCI;

Arrhythmia AE caused by the Impella ECP™ that met the protocol definition of a sustained arrhythmia or resulted in hemodynamic compromise; or Arrhythmia resulting in device removal.

Of the 256 subjects in the Impella ECP™ Pivotal study, 59 subjects (23.0%) had a site-reported arrhythmia AE, with 42 of those subjects (16%) experiencing the arrhythmia AE event between the time of vascular access and device removal. However, only 6 (2.3%) of all subjects in the Impella ECP™ Pivotal study experienced an arrhythmia AE requiring intervention. One subject required device repositioning during the PCI, and five additional subjects met the protocol definition of sustained arrhythmia or experienced hemodynamic compromise requiring inotropes or vasopressor support. Among these five subjects, only one (0.4%) required defibrillation. The Impella ECP™ was never removed and replaced with a new Impella ECP™ due to arrhythmia during the Impella ECP™ Pivotal study.

As illustrated in FIG. 7, overall, 57% (145/256) of patients were reported to have some degree of bigeminy or ectopy during the procedure. Given the majority of these events did not rise to level of a site-reported AE, these most likely were nuisance arrhythmias often seen when introducing devices into the arrhythmogenic left ventricle. Additionally, while 23% (59/256) of subjects had an arrhythmia event rising to the level of a site-reported AE, only 16% (42/256) of subjects experienced that event from the time of vascular access through device removal. This rate reduces to just 2.3% (6/256) when considering events that occurred during the PCI itself and required physician intervention such as device repositioning or need for cardioversion or resulted in hemodynamic compromise requiring inotropic or vasopressor support.

Results-Clinically Significant Arrhythmia Adverse Event (AE):

A clinically significant arrhythmia adverse event (AE) associated with the mechanical circulatory support device, i.e., the Impella ECP™ pump device, experiencing the arrhythmia event between the time of vascular access with the mechanical circulatory support device and removal of the mechanical circulatory support device from the vasculature is approximately 2.3%.

CONCLUSION

The Impella ECP™ study demonstrated the benefits of a smaller access site for a percutaneous blood pump for the high-risk PCI population studied. The Impella ECP™ may provide support while providing an acceptable rate of MACCE for the high-risk PCI population studied. The observed rate of MACCE was much lower than the established performance goal based on other hemodynamic support devices. Further, no signal of concern was seen regarding death, bleeding, and vascular complications with this device.

The Impella ECP™ device further demonstrated the feasibility of crossing the aortic valve in approximately one minute without using a guidewire resulting in no aortic valve injuries. Hemocompatibility was observed as no major hemolysis was reported. While ventricular arrhythmias were seen in this study, the majority did not warrant any intervention. Also, the length of stay—from admission through discharge—was only a mean of 3.5 days, which was much shorter than in other studies, and further supports the benefit of the smaller access.

Overall, the study demonstrated that Impella ECP™ can be used to achieve acceptable 30-day MACCE rates in the high-risk PCI population as seen with other hemodynamic support devices and can do so with a potentially lower rate of bleeding and vascular complications and shorter length of stay. In fact, the rate of MACCE was much lower than what was considered an acceptable rate of MACCE.

While ventricular arrhythmias were observed in the Impella ECP™ Pivotal study, the rates of both protocol-defined sustained arrhythmias and arrhythmias requiring intervention were comparable to rates of ventricular arrhythmias of similar severity previously observed in Impella- and IABP-supported HRPCI. This rate may represent the baseline rate of arrhythmia or arrhythmia requiring treatment in this population, regardless of the use of the Impella ECP™.

The following are exemplary aspects of the disclosure.

Aspect 1. A method of providing ventricular support for a human patient during a high-risk percutaneous coronary intervention procedure, the method comprising:
inserting a mechanical circulatory support device into the vasculature of a human patient, the mechanical circulatory support device being movable between a compressed state and an expanded state;
delivering the mechanical circulatory support device within the vasculature into a heart of the human patient;
operating the mechanical circulatory support device for a support period of up to 6 hours; and
wherein a 30-day rate of incidence of a major adverse cardiovascular and cerebrovascular event ("MACCE") associated with the mechanical circulatory support device is approximately 5.9% to approximately 12.9%.

Aspect 2. The method of aspect 1, wherein the 30-day rate of incidence MACCE is approximately 6.3%.

Aspect 3. The method of aspect 1, wherein the 30-day rate of incidence of MACCE is approximately 5.9% to approximately 8.9%.

Aspect 4. The method of aspect 1, wherein the 30-day rate of incidence of MACCE is approximately 6.3% to approximately 9.5%.

Aspect 5. A method, comprising:
for each of a plurality of human patients:
inserting a mechanical circulatory support device into the vasculature of said patient, the mechanical circulatory device being movable between a compressed state and an expanded state;
delivering the mechanical circulatory support device within the vasculature into a heart of said patient;
operating the mechanical circulatory support device for a support period of up to 6 hours; and
determining whether said patient experiences an incidence of a major adverse cardiovascular and cerebrovascular event ("MACCE") during an assessment period beginning from the insertion of the mechanical circulatory support device into the vasculature of each of said patients through about 30 days after the high-risk percutaneous coronary intervention procedure; and
wherein the composite rate of MACCE in the plurality of human patients is approximately 12.9% to approximately 16.9%.

Aspect 6. The method of aspect 5, wherein the composite rate of MACCE in the plurality of human patients is approximately 12.9% to approximately 16.3%.

Aspect 7. The method of aspects 1-6, wherein the mechanical circulatory support device comprises a housing, a drive shaft rotatably mounted within the housing and a rotor being connected to the drive shaft.

Aspect 8. The method of aspect 7, wherein both the housing and the rotor are movable between the compressed state and the expanded state.

Aspect 9. The method of aspect 8, wherein the housing in the compressed state has an outer diameter of about 3.0 mm (9 French).

Aspect 10. The method of aspect 8, wherein the housing in the expanded state has an outer diameter of about 7.0 mm (21 French).

Aspect 11. The method of aspects 1-6, further comprising a motor being connected to the drive shaft, the motor being disposed external to each of the plurality of human patients.

Aspect 12. The method of aspects 1-6, wherein, before the inserting a mechanical circulatory support device step, inserting a delivery assist device into the vasculature of each of the human patients.

Aspect 13. The method of aspects 1-6, wherein the number of plurality of human patients is 238 patients.

Aspect 14. The method of aspects 1-6, wherein, during the operating step, the mechanical circulatory support device is in the heart spanning from the left ventricle through the aortic valve and into the aorta.

Aspect 15. The method of aspects 1-6, wherein mechanical circulatory support device has a blood flow inlet in the left ventricle and a blood flow outlet in the aorta.

Aspect 16. A method of providing ventricular support for a human patient during a high-risk percutaneous coronary intervention procedure, the method comprising:

inserting a mechanical circulatory support device into the vasculature of a human patient, the mechanical circulatory support device being movable between a compressed state and an expanded state;

delivering, with the aid of the delivery assist device, the mechanical circulatory support device into a heart of the human patient;

operating the mechanical circulatory support device for a support period of up to 6 hours; and wherein a 30-day bleeding rate associated with the mechanical circulatory support device is approximately 4.3% to approximately 5.9%.

Aspect 17. The method of aspects 16, wherein the bleeding rate is approximately 5.9%.

Aspect 18. The method of aspect 16, wherein the mechanical circulatory support device comprises a housing, a drive shaft rotatably mounted within the housing and a rotor being connected to the drive shaft, the mechanical circulatory support device being movable between a compressed state and a expanded state.

Aspect 19. The method of aspect 18, wherein both the housing and the rotor are movable between the compressed state and the expanded state.

Aspect 20. The method of aspect 19, wherein the housing in the compressed state has an outer diameter of about 3.0 mm (9 French).

Aspect 21. The method of aspect 20, wherein the housing in the expanded state has an outer diameter of about 7.0 mm (21 French).

Aspect 22. The method of aspect 16, further comprising a motor being connected to the drive shaft, the motor being disposed external to said patient.

Aspect 23. The method of aspect 16, wherein, before the inserting a mechanical circulatory support device step, inserting a delivery assist device into the vasculature of said patient.

Aspect 25. The method of Aspect 16, wherein, during the operating step, the mechanical circulatory support device is in the heart spanning from the left ventricle through the aortic valve and into the aorta.

Aspect 26. The method of Aspect 25, wherein the mechanical circulatory support device has a blood flow inlet in the left ventricle and a blood flow outlet in the aorta.

Aspect 27. A method of providing ventricular support for a human patient during a high-risk percutaneous coronary intervention procedure, the method comprising:

inserting a mechanical circulatory support device into the vasculature of a human patient, the mechanical circulatory support device being movable between a compressed state and an expanded state;

delivering, with the aid of a delivery assist device, the mechanical circulatory support device into a heart of the human patient;

operating the mechanical circulatory support device for a support period; and wherein a sustained arrhythmia event associated with the mechanical circulatory support device is approximately 2.7%.

Aspect 28. The method of aspect 27, wherein the operating step occurs up to about 6 hours.

Aspect 29. The method of aspects 1-28, wherein the operating the mechanical circulatory support device step occurs between approximately 19 minutes and approximately 209 minutes.

Aspect 30. The method of aspect 29, wherein the operating the mechanical circulatory support device step occurs for approximately 77 minutes.

Aspect 31. The method of aspect 30, wherein the operating the mechanical circulatory support device step occurs for approximately 77 minutes with a standard deviation of 35.5 minutes.

Aspect 32. The method of aspects 1-31, wherein the delivering the mechanical circulatory support device step takes approximately 1.3 minutes to approximately 3.4 minutes from entering the vasculature to crossing an aortic valve of the heart.

Aspect 33. The method of aspects 1-32, further comprising placing the human patient under fluoroscopy from approximately 21 minutes to approximately 54 minutes.

Aspect 34. A method of use comprising:

reducing a length of a hospital stay for a group of human patients undergoing a high-risk percutaneous coronary intervention procedure using a mechanical circulatory support device from admission to discharge to approximately 3.6 days.

Aspect 35. The method of aspect 34 wherein the length of the hospital stay was 1 day for 44% of the group of human patients.

Aspect 36. The method of aspect 34 wherein the length of the hospital stay was less than or equal to 5 days for 77% of the group of human patients.

Aspect 37. A method of use comprising:

reducing a length of a time to a procedure for a group of human patients undergoing a high-risk percutaneous coronary intervention procedure using a mechanical circulatory support device from admission to procedure to approximately less than 24 hours for 63.7% of the group of human patients.

Aspect 38. A method of use comprising:

reducing a length of a time to a procedure for a group of human patients undergoing a high-risk percutaneous coronary intervention procedure using a mechanical circulatory support device from admission to procedure to less than or equal to five (5) days for 87.9% of the group of human patients.

Aspect 39. A method of use comprising:

reducing a length of a hospital stay for a group of human patients undergoing a high-risk percutaneous coronary intervention procedure using a mechanical circulatory support device from the procedure to discharge to approximately 1.9 days.

Aspect 40. The method of aspect 39 wherein the length of the hospital stay was 1 day for 60.9% of the group of human patients.

Aspect 41. The method of aspect 39 wherein the length of the hospital stay was less than or equal to 2 days for 79.7% of the group of human patients.

Aspect 42. The method of aspects 34-41, further comprising:

inserting the mechanical circulatory support device into the vasculature of a human patient of the group of patients;

delivering the mechanical circulatory support device within the vasculature into a heart of the human patient; and operating the mechanical circulatory support device.

Aspect 43. The method of aspect 42, wherein the mechanical circulatory support device comprises a housing, a drive shaft rotatably mounted within the housing and a rotor being connected to the drive shaft, the mechanical circulatory support device being movable between a compressed state and a expanded state.

Aspect 44. The method of aspect 43, wherein both the housing and the rotor are movable between the compressed state and the expanded state.

Aspect 45. The method of aspect 44, wherein the housing in the compressed state has an outer diameter of about 3.0 mm (9 French).

Aspect 46. The method of aspect 44, wherein the housing in the expanded state has an outer diameter of about 7.0 mm (21 French).

Aspect 47. The method of aspect 42, further comprising a motor being connected to the drive shaft, the motor being disposed external to the respective human patient.

Aspect 48. The method of aspect 42, wherein the mechanical circulatory support device step further comprises inserting a delivery assist device into the vasculature of the human patient.

Aspect 49. The method of aspects 34-42, wherein the number of plurality of human patients is 238 patients.

Aspect 50. The method of aspects 42, wherein, during the operating step, the mechanical circulatory support device is in the heart spanning from the left ventricle through the aortic valve and into the aorta.

Aspect 51. The method of aspects 42, wherein the mechanical circulatory support device has a blood flow inlet in the left ventricle and a blood flow outlet in the aorta.

Aspect 52. The method of aspects 1-51, wherein the mechanical circulatory support device includes a distal bearing that comprises a heat conducting part configured to enable heat transfer away from the distal bearing.

Aspect 53. The method of aspects 1-51, further comprising a crimp tool for crimping the mechanical circulatory support device into the first radially compressed state for transfer into a tubular sheath, the crimp tool comprising:

an elongated tube that defines a tapered longitudinal bore, the bore being at least about 30 mm long and having an inside dimension that tapers along the length of the bore from (a) at least about a maximum outside dimension of the pump at a distal end of the bore to (b) about an inside dimension of the tubular sheath at a proximal end of the bore.

Aspect 54. The method of aspect 53, further comprising disposing the mechanical circulatory support device inside a distal end of the tapered longitudinal tube of the elongated tube, the tube bore being at least about 30 mm long and having an inside dimension that tapers along the length of the tube bore from (a) at least about a maximum outside dimension of the mechanical circulatory support device at the distal end of the tube bore to (b) at most about 4 mm in diameter at a proximal end of the tube bore; and translating the mechanical circulatory support device through the tube bore in a direction toward the proximal end of the tube bore, including contacting an outside surface of the mechanical circulatory support device with an inside surface of the elongated tube as the mechanical circulatory support device translates through the tube bore, thereby collapsing the mechanical circulatory support device into the compressed state.

Aspect 55. The method of aspects 1-54, wherein the rotor comprising at least one rotor blade, a hub, and an axis of rotation, wherein at least a portion of the at least one rotor blade extends from the hub along a first axis that is offset a predetermined distance from a radial axis of the rotor that traverses the axis of rotation.

Aspect 56. The method of aspects 7-54, wherein the drive shaft comprising an outer layer of wound or braided wires, an inner layer of wound or braided wires, and a reinforcement element arranged within at least the outer layer of wound or braided wires, the drive shaft is rotatably supported in a proximal bearing located proximal of the rotor and a distal bearing located distal of the rotor, the reinforcement element extends from at least a point within the proximal bearing to a point within the distal bearing.

Aspect 57. A method, comprising:

for each of a plurality of human patients:

inserting a mechanical circulatory support device at an insertion site into the vasculature of said patient, the mechanical circulatory support device being movable between a compressed state and an expanded state;

delivering, with the aid of the delivery assist device, the mechanical circulatory support device into a heart of said patient;

operating the mechanical circulatory support device for a support period;

removing the mechanical circulatory support device from the vasculature of the human patient;

closing the insertion site with an 8 French or smaller bioabsorbable closure device;

determining whether said patient had a successful first closure of the insertion site; and wherein a rate of successful first closure of the insertion site is identified for the plurality of human patients is approximately 92%.

Aspect 58. The method of aspect 57, wherein the operating step occurs up to about 6 hours.

Aspect 59. The method of aspect 57, wherein the bioabsorbable closure device comprises collagen.

Aspect 60. A method, comprising:

for each of a plurality of human patients:

inserting a mechanical circulatory support device into the vasculature of said patient, the mechanical circulatory support device being movable between a compressed state and an expanded state;

delivering, with the aid of a delivery assist device, the mechanical circulatory support device into a heart of said patient;

operating the mechanical circulatory support device for a support period;

determining whether said patient experiences a sustained arrhythmia; and wherein a sustained arrhythmia event occurred in approximately 2.7% of the plurality of human patients.

Aspect 61. A method, comprising:

for each of a plurality of human patients:

inserting a mechanical circulatory support device into the vasculature of said patient, the mechanical circulatory support device being movable between a compressed state and an expanded state;

delivering, with the aid of the delivery assist device, the mechanical circulatory support device into a heart of said patient;

operating the mechanical circulatory support device for a support period of up to 6 hours;

determining a bleeding rate of said patient; and wherein the bleeding rate is approximately 4.3% to approximately 5.9%.

Aspect 62. The method of aspect 61, wherein the bleeding rate of said patient is determined during an assessment period beginning from the insertion of the mechanical circulatory support device into the vasculature of said patient through about 30 days after the high-risk percutaneous coronary intervention procedure.

Aspect 63. The method of aspect 61, wherein the number of the plurality of human patients is 238 patients.

Aspect 64. A method of providing ventricular support for a human patient during a high-risk percutaneous coronary intervention procedure, the method comprising:

inserting a mechanical circulatory support device at an insertion site into the vasculature of a human patient, the mechanical circulatory support device being movable between a compressed state and an expanded state;

delivering, with the aid of the delivery assist device, the mechanical circulatory support device into a heart of the human patient;

operating the mechanical circulatory support device for a support period;

removing the mechanical circulatory support device from the vasculature of the human patient;

closing the insertion site with an 8 French or smaller bioabsorbable closure device;

wherein a rate of successful first closure of the insertion site associated with the mechanical circulatory support device is approximately 92%.

Aspect 65. A method of providing ventricular support for a human patient during a high-risk percutaneous coronary intervention procedure, the method comprising:

inserting a mechanical circulatory support device into the vasculature of a human patient, the mechanical circulatory support device being movable between a compressed state and an expanded state;

delivering, with the aid of a delivery assist device, the mechanical circulatory support device into a heart of the human patient;

operating the mechanical circulatory support device for a support period; and wherein a clinically significant arrhythmia adverse event (AE) associated with the mechanical circulatory support device experiencing the arrhythmia event between the time of vascular access with the mechanical circulatory support device and removal of the mechanical circulatory support device from the vasculature is approximately 2.3%.

Aspect 66. The method of aspect 65, wherein the operating step occurs up to about 6 hours.

Aspect 67. The method of aspect 65, wherein the mechanical circulatory support device is in the expanded state during the operating the mechanical circulatory support device step.

Aspect 68. The method of aspects 66, wherein the operating the mechanical circulatory support device step occurs between approximately 19 minutes and approximately 209 minutes.

Aspect 69. The method of aspect 68, wherein the operating the mechanical circulatory support device step occurs for approximately 77 minutes.

Aspect 70. The method of aspect 69, wherein the operating the mechanical circulatory support device step occurs for approximately 77 minutes with a standard deviation of 35.5 minutes.

Aspect 71. The method of aspects 65, wherein the delivering the mechanical circulatory support device step takes approximately 1.3 minutes to approximately 3.4 minutes from entering the vasculature to crossing an aortic valve of the heart.

Aspect 72. The method of aspects 65, further comprising placing the human patient under fluoroscopy from approximately 21 minutes to approximately 54 minutes.

Aspect 73. The method of aspects 65, wherein the mechanical circulatory support device is in the compressed state during the delivering the mechanical circulatory support device step from enring the vasculature to crossing an aortic valve of the heart.

Aspect 74. A mechanical circulatory support system for reducing a clinically significant arrhythmia adverse event (AE) in a high-risk percutaneous coronary intervention (PCI) procedure, the system comprising:

a catheter comprising a proximal end and a distal end;

a radially expandable blood pump positioned at the distal end of the catheter, wherein the blood pump is configured to transition between a first compressed state with an outer diameter of approximately 3.0 mm (9 French) and a second expanded state with an outer diameter of approximately 7.0 mm (21 French);

a controller operably connected to the motor, the controller configured to control the rotational speed of the blood pump; and wherein a clinically significant arrhythmia AE associated with the mechanical circulatory support device is approximately 2.3% between the time of vascular access with the blood pump and removal of blood pump from the vasculature.

Aspect 75. A method of operating a mechanical circulatory support system to optimize patient outcomes during a high-risk percutaneous coronary intervention (PCI) procedure, the method comprising:

inserting a radially expandable intravascular blood pump through an introducer sheath positioned in the femoral artery, the radially expandable intravascular blood pump operably connected to a controller;

advancing the blood pump across the aortic valve and into the left ventricle without using a guidewire;

operating, via the controller, an extracorporeal motor configured to control the rotational speed of the blood pump;

wherein a clinically significant arrhythmia AE associated with the mechanical circulatory support device is approximately 2.3% between the time of vascular access with the blood pump and removal of blood pump from the vasculature.

Aspect 76. The mechanical circulatory support system in accordance with aspect 74, wherein the controller further comprises at least one control element configured to receive user input.

Aspect 77. The mechanical circulatory support system in accordance with aspect 76 wherein the controller is further configured to control the rotational speed of the blood pump in response to receiving user input.

Aspect 78. The method in accordance with aspect 75, wherein the controller further comprises at least one control element configured to receive user input.

Aspect 79. The method in accordance with aspect 78, wherein the controller is further configured to control the rotational speed of the blood pump in response to receiving user input.

Aspect 80. The method in accordance with aspect 75, further comprising:

receiving, from the blood pump, data associated with operation of the blood pump; and displaying, on the controller, an indication of the data.

Aspect 81. The method in accordance with aspect 75, further comprising:

terminating circulatory support within a pre-defined operational period, wherein the length of hospital stay from admission to discharge is reduced to an average of approximately 3.5 days.

Aspect 82. A mechanical circulatory support system for reducing major adverse cardiovascular and cerebrovascular events (MACCE) in a high-risk percutaneous coronary intervention (PCI) procedure, the system comprising:

a catheter comprising a proximal end and a distal end;

a radially expandable blood pump positioned at the distal end of the catheter, wherein the blood pump is configured to transition between a first compressed state with an outer diameter of approximately 3.0 mm (9 French) and a second expanded state with an outer diameter of approximately 7.0 mm (21 French);

an extracorporeally positioned motor;

a controller operably connected to the motor, the controller configured to control the rotational speed of the blood pump; and wherein a 30-day rate of incidence of a MACCE associated with the mechanical circulatory support device is approximately 5.9% to approximately 12.9%.

Aspect 83. A method of operating a mechanical circulatory support system to optimize patient outcomes during a high-risk percutaneous coronary intervention (PCI) procedure, the method comprising:

inserting a radially expandable intravascular blood pump through an introducer sheath positioned in the femoral artery, the radially expandable intravascular blood pump operably connected to a controller;

advancing the blood pump across the aortic valve and into the left ventricle without using a guidewire;

operating, via the controller, an extracorporeal motor configured to control the rotational speed of the blood pump;

wherein a 30-day rate of incidence of a MACCE associated with the mechanical circulatory support device is approximately 5.9% to approximately 12.9%.

Aspect 84. The mechanical circulatory support system in accordance with aspect 82, wherein the controller further comprises at least one control element configured to receive user input.

Aspect 85. The mechanical circulatory support system in accordance with aspect 84, wherein the controller is further configured to control the rotational speed of the blood pump in response to receiving user input.

Aspect 86. The method in accordance with aspect 83, wherein the controller further comprises at least one control element configured to receive user input.

Aspect 87. The method in accordance with aspect 86, wherein the controller is further configured to control the rotational speed of the blood pump in response to receiving user input.

Aspect 88. The method in accordance with aspect 83, further comprising:

receiving, from the blood pump, data associated with operation of the blood pump; and displaying, on the controller, an indication of the data.

Aspect 89. The method in accordance with aspect 83, further comprising:

terminating circulatory support within a pre-defined operational period, wherein the length of hospital stay from admission to discharge is reduced to an average of approximately 3.5 days.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A method of providing ventricular support for a human patient during a high-risk percutaneous coronary intervention procedure, the method comprising:

inserting a mechanical circulatory support device into the vasculature of a human patient, the mechanical circulatory support device being movable between a compressed state having an outer diameter of approximately 9 French (Fr) and an expanded state having an outer diameter of approximately 21 Fr;

delivering, with the aid of a delivery assist device, the mechanical circulatory support device into a heart of the human patient, while in the compressed state;

operating the mechanical circulatory support device for a support period at up to a maximum flow rate of approximately 4.4 L/min, while in the expanded state; and achieving a risk of a clinically significant arrhythmia adverse event (AE) associated with the mechanical circulatory support device experiencing the arrhythmia event between the time of vascular access with the mechanical circulatory support device and removal of the mechanical circulatory support device from the vasculature is approximately 2.3%.

2. The method of claim 1, wherein the operating step occurs up to about 6 hours.

3. The method of claim 1, wherein the mechanical circulatory support device is in the compressed state during the delivering the mechanical circulatory support device step from entering the vasculature to crossing an aortic valve of the heart.

4. The method of claim 1, further comprising a motor being connected to a drive shaft of the mechanical circulatory support device, the motor being disposed external to the human patient.

5. The method of claim 1, wherein the clinically significant arrhythmia adverse event (AE) is an event occurring in a patient having an arrhythmia during the time from vascular access through device removal and having one of the following:

Arrhythmia AE requiring repositioning of the mechanical circulatory support device during a percutaneous coronary intervention (PCI) procedure;

Arrhythmia AE caused by the mechanical circulatory support device that met the definition of a sustained arrhythmia or resulted in hemodynamic compromise; or Arrhythmia resulting in mechanical circulatory support device removal.

6. A method, comprising:

for each of a plurality of human patients:

inserting a mechanical circulatory support device into the vasculature of said patient, the mechanical circulatory support device being movable between a compressed state having an outer diameter of approximately 9 French (Fr) and an expanded state having an outer diameter of approximately 21 Fr;

delivering, with the aid of a delivery assist device, the mechanical circulatory support device into a heart of said patient, while in the compressed state;

operating the mechanical circulatory support device for a support period at up to a maximum flow rate of approximately 4.4 L/min, while in the expanded state; and achieving a risk of a clinically significant arrhythmia adverse event (AE) percentage associated with the mechanical circulatory support device experiencing the arrhythmia event between the time of vascular access with the mechanical circulatory support device and removal of the mechanical circulatory support device from the vasculature of approximately 2.3%.

7. The method of claim 6, wherein the operating step occurs up to about 6 hours.

8. The method of claim 7, wherein the operating the mechanical circulatory support device step occurs between approximately 19 minutes and approximately 209 minutes.

9. The method of claim 6, wherein the delivering the mechanical circulatory support device step takes approximately 1.3 minutes to approximately 3.4 minutes from entering the vasculature to crossing an aortic valve of the heart.

10. The method of claim 6, further comprising monitoring whether the patient experiences an arrhythmia.

11. The method of claim 6, wherein the mechanical circulatory support device is in the compressed state during the delivering the mechanical circulatory support device step from entering the vasculature to crossing an aortic valve of the heart.

12. The method of claim 6, further comprising a motor being connected to a drive shaft of the mechanical circulatory support device, the motor being disposed external to the respective human patient.

13. The method of claim 6, wherein the clinically significant arrhythmia adverse event (AE) is an event occurring in a patient having an arrhythmia during the time from vascular access through device removal and having one of the following:

Arrhythmia AE requiring repositioning of the mechanical circulatory support device during a percutaneous coronary intervention (PCI) procedure;

Arrhythmia AE caused by the mechanical circulatory support device that met the definition of a sustained arrhythmia or resulted in hemodynamic compromise; or Arrhythmia resulting in mechanical circulatory support device removal.

* * * * *